US 7,390,495 B2

(12) United States Patent
Despres et al.

(10) Patent No.: US 7,390,495 B2
(45) Date of Patent: Jun. 24, 2008

(54) NEUROVIRULENT STRAIN OF THE WEST NILE VIRUS AND USES THEREOF

(75) Inventors: Philippe Despres, La Garenne-Colombes (FR); Vincent Deubel, Vanves (FR); Jean-Louis Guenet, Longjumeau (FR); Marie-Therese Drouet, Plaisir (FR); Mertyn Malkinson, Beit Dagan (IL); Caroline Banet, Beit Dagan (IL); Marie-Pascale Frenkiel, Levallois (FR); Marie-Pierre Courageot, Paris (FR); Fasseli Coulibaly, Saint-Maur (FR); Adeline Catteau, Savigny sur Orge (FR); Marie Flamand, New York, NY (US); Patrick Weber, Montreuil (FR); Pierre-Emmanuel Ceccaldi, Boissise-la-bertrand (FR)

(73) Assignees: Institut Pasteur, Paris (FR); Kimron Veterinary Institute, Beit Dagan (IL)

( * ) Notice: Subject to any disclaimer, the term of this patent is extended or adjusted under 35 U.S.C. 154(b) by 164 days.

(21) Appl. No.: 10/956,085

(22) Filed: Oct. 4, 2004

(65) Prior Publication Data

US 2005/0164170 A1   Jul. 28, 2005

Related U.S. Application Data

(63) Continuation of application No. 10/474,186, filed as application No. PCT/FR02/01168 on Apr. 4, 2002, now abandoned.

(30) Foreign Application Priority Data

Apr. 4, 2001 (FR) .................................. 01 04599
Sep. 6, 2001 (FR) .................................. 01 11525

(51) Int. Cl.
*A61K 39/12* (2006.01)
*C12N 7/00* (2006.01)
*A61K 39/02* (2006.01)

(52) U.S. Cl. .................................. 424/218.1; 435/235.1
(58) Field of Classification Search ....................... None
See application file for complete search history.

(56) References Cited

U.S. PATENT DOCUMENTS

2005/0164170 A1   7/2005   Despres et al.

OTHER PUBLICATIONS

Urosevic et al., Molecular characterization of virus-specific RNA produced in the brains of flavivirus-susceptible and -resistant mice after challenge with Murray Valley encephalitis virus, 1997, Journal of General Virology, vol. 78, pp. 23-29.*
Platonov et al., Out break of West Nile Virus Infection, Volgograd Region, Russia, 1999, 2001, Emerging Infectious Diseases, vol. 7, No. 1, pp. 128-132.*
Malkinson et al., Introduction of West Nile Virus in the Middle East by Migrating White Storks, 2002, Emerging Infectious Diseases, vol. 8, No. 4, pp. 392-327.*
X-Y Jia, et al.: "Genetic analysis of West Nile New York 1999 encephalitis virus" Lancet, XX, XX, vol. 354, No. 9194, pp. 1971-1972, Dec. 4, 1999.
RS Lanciotti et al., "Orgin of the West Nile virus responsible for an outbreak of encephalitis in the northeastern United States" Science (Washington DC), vol. 286, No. 5448, pp. 2333-2337, Dec. 17, 1999.
John F. Anderson, et al., "Isolation of West Nile virus from mosquitoes, crows, and a Cooper's hawk in Connecticut" Science (Washington DC), vol. 286, No. 5448, pp. 2331-2333, Dec. 17, 1999.
G. Wengler, et al., "An analysis of the antibody response against West Nile virus E protein purified by SDS-page indicates that this protein does not contain sequential epitopes for efficient induction of neutralizingantibodies" Journal of Genral Virology, vol. 70, No. 4, pp. 987-992, 1989.
U.S. Appl. No. 11/614,414, filed Dec. 21, 2006, Despres et al.

* cited by examiner

*Primary Examiner*—Bruce Campell
*Assistant Examiner*—Benjamin P. Blumel
(74) *Attorney, Agent, or Firm*—Oblon, Spivak, McClelland, Maier & Neustadt, P.C.

(57) ABSTRACT

Neuroinvasive and neurovirulent strain of the West Nile virus, named IS-98-ST1, nucleic acid molecules derived from its genome, proteins and peptides encoded by said nucleic acid molecules, and uses thereof.

6 Claims, 13 Drawing Sheets

Figure 4:
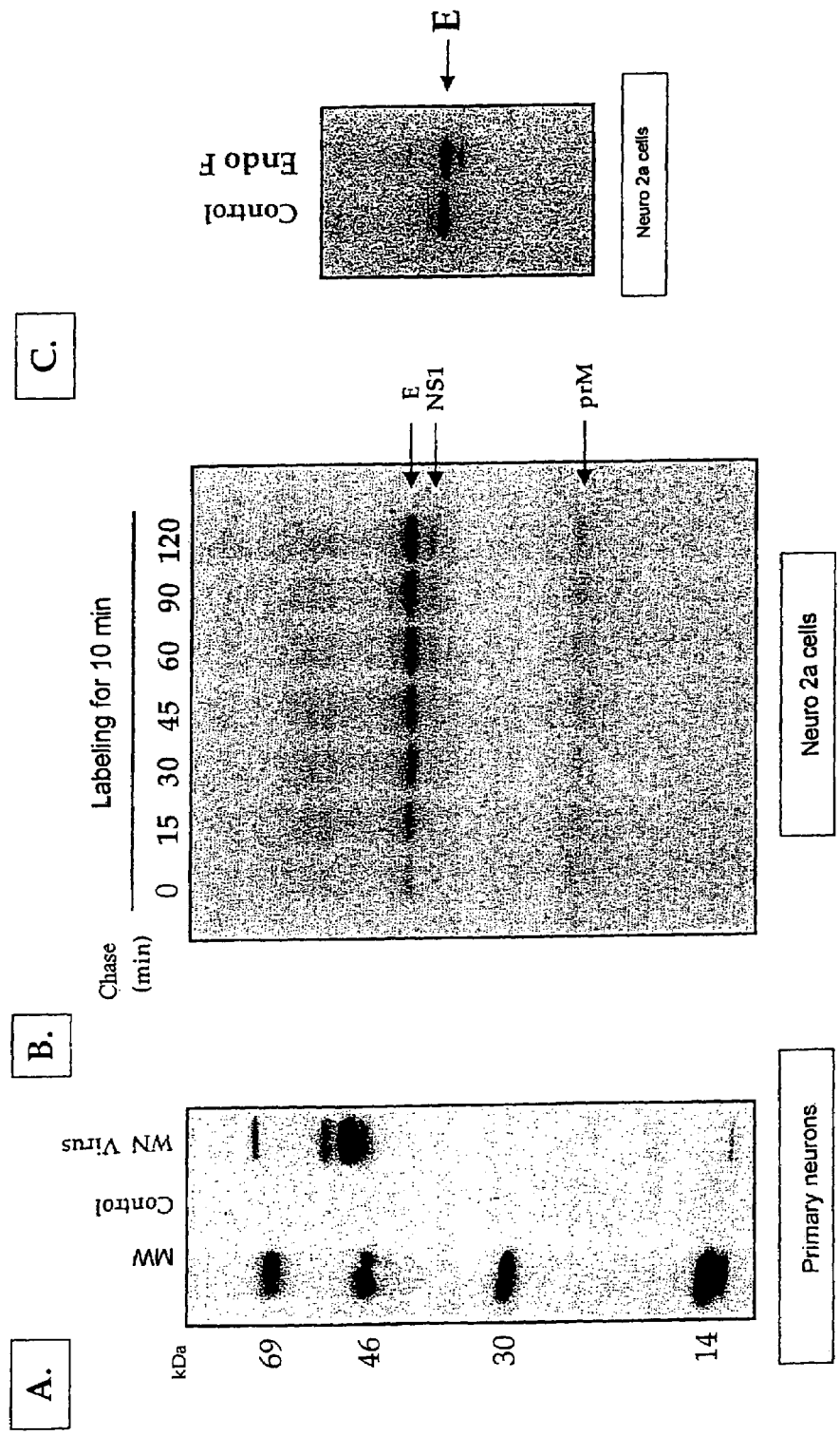

```
                    C
CI      MSKKPGGPGKSRAVNMLKRGMPRVLSLIGLKRAMLSLIDGKGPIRFVLAL
FLA     MSKKPGGPGKSRAVNMLKRGMPRVLSLIGLKRAMLSLIDGKGPIRFVLAL
        **************************************************

CI      LAFFRFTAIAPTRAVLDRWRGVNKQTAMKHLLSFKKELGTLTSAINRRSS
FLA     LAFFRFTAIAPTRAVLDRWRGVNKQTAMKHLLSFKKELGTLTSAINRRSS
        **************************************************
                                prM
CI      KQKKRGGKTGIAVMIGLIASVGAVTLSNFQGKVMMTVNATDVTDVITIPT
FLA     KQKKRGGKTGIAVMIGLIASVGAVTLSNFQGKVMMTVNATDVTDVITIPT
        **************************************************

CI      AAGKNLCIVRAMDVGYMCDDTITYECPVLSAGNDPEDIDCWCTKSAVYVR
FLA     AAGKNLCIVRAMDVGYMCDDTITYECPVLSAGNDPEDIDCWCTKSAVYVR
        **************************************************
                    M
CI      YGRCTKTRHSRRSRRSLTVQTHGESTLANKKGAWMDSTKATRYLVKTESW
FLA     YGRCTKTRHSRRSRRSLTVQTHGESTLANKKGAWMDSTKATRYLVKTESW
        **************************************************
                                                    E
CI      ILRNPGYALVAAVIGWMLGSNTMQRVVFVVLLLLVAPAYSFNCLGMSNRD
FLA     ILRNPGYALVAAVIGWMLGSNTMQRVVFVVLLLLVAPAYSFNCLGMSNRD
        **************************************************

CI      FLEGVSGATWVDLVLEGDSCVTIMSKDKPTIDVKMMNMEAANLAEVRSYC
FLA     FLEGVSGATWVDLVLEGDSCVTIMSKDKPTIDVKMMNMEAVNLAEVRSYC
        ****************************************  ********

CI      YLATVSDLSTKAACPTMGEAHNDKRADPAFVCRQGVVDRGWGNGCGLFGK
FLA     YLATVSDLSTKAACPTMGEAHNDKRADPAFVCRQGVVDRGWGNGCGLFGK
        **************************************************

CI      GSIDTCAKFACSTKAIGRTILKENIKYEVAIFVHGPTTVESHGNYSTQVG
FLA     GSIDTCAKFACSTKAIGRTILKENIKYEVAIFVHGPTTVESHGNYSTQVG
        **************************************************

CI      ATQAGRFSITPAAPSYTLKLGEYGEVTVDCEPRSGIDTNAYYVMTVGTKT
FLA     ATQAGRFSITPAAPSYTLKLGEYGEVTVDCEPRSGIDTNAYYVMTVGTKT
        **************************************************

CI      FLVHREWFMDLNLPWSSAGSTVWRNRETLMEFEEPHATKQSVIALGSQEG
FLA     FLVHREWFMDLNLPWSSAGSTVWRNRETLMEFEEPHATKQSVIALGSQEG
        **************************************************

CI      ALHQALAGAIPVEFSSNTVKLTSGHLKCRVKMEKLQLKGTTYGVCSKAFK
FLA     ALHQALAGAIPVEFSSNTVKLTSGHLKCRVKMEKLQLKGTTYGVCSKAFK
        **************************************************

CI      FLGTPADTGHGTVVLELQYTGTDGPCKVPISSVASLNDLTPVGRLVTVNP
FLA     FLGTPADTGHGTVVLELQYTGTDGPCKVPISSVASLNDLTPVGRLVTVNP
        **************************************************

CI      FVSVATANAKVLIELEPPFGDSYIVVGRGEQQINHHWHKSGSSIGKAFTT
FLA     FVSVATANAKVLIELEPPFGDSYIVVGRGEQQINHHWHKSGSSIGKAFTT
        **************************************************
```

FIG. 1A

```
CI   TLKGAQRLAALGDTAWDFGSVGGVFTSVGKAVHQVFGGAFRSLFGGMSWI
FLA  TLKGAQRLAALGDTAWDFGSVGGVFTSVGKAVHQVFGGAFRSLFGGMSWI
     **************************************************
                                                      NS1
CI   TQGLLGALLLWMGINARDRSIALTFLAVGGVLLFLSVNVHADTGCAIDIS
FLA  TQGLLGALLLWMGINARDRSIALTFLAVGGVLLFLSVNVHADTGCAIDIS
     **************************************************

CI   RQELRCGNGVFIHNDVEAWMDRYKYYPETPQGLAKIIQKAHKEGVCGLRS
FLA  RQELRCGSGVFIHNDVEAWMDRYKYYPETPQGLAKIIQKAHKEGVCGLRS
     ******* ******************************************

CI   VSRLEHQMWEAVKDELNTLLKENGVDLSVVVEKQEGMYKSAPKRLTATTE
FLA  VSRLEHQMWEAVKDELNTLLKENGVDLSVVVEKQEGMYKSAPKRLTATTE
     **************************************************

CI   KLEIGWKAWGKSILFAPELANNTFVVDGPETKECPTQNRAWNSLEVEDFG
FLA  KLEIGWKAWGKSILFAPELANNTFVVDGPETKECPTQNRAWNSLEVEDFG
     **************************************************

CI   FGLTSTRMFLKVRESNTTECDSKIIGTAVKNNLAIHSDLSYWIESRLNDT
FLA  FGLTSTRMFLKVRESNTTECDSKIIGTAVKNNLAIHSDLSYWIESRLNDT
     **************************************************

CI   WKLERAVLGEVKSCTWPETHTLWGDGILESDLIIPVTLAGPRSNHNRRPG
FLA  WKLERAVLGEVKSCTWPETHTLWGDGILESDLIIPVTLAGPRSNHNRRPG
     **************************************************

CI   YKTQNQGPWDEGRVEIDFDYCPGTTVTLSESCGHRGPATRTTTESGKLIT
FLA  YKTQNQGPWDEGRVEIDFDYCPGTTVTLSESCGHRGPATRTTTESGKLIT
     **************************************************
                                                      NS2A
CI   DWCCRSCTLPPLRYQTDSGCWYGMEIRPQRHDEKTLVQSQVNAYNADMID
FLA  DWCCRSCTLPPLRYQTDSGCWYGMEIRPQRHDEKTLVQSQVNAYNADMID
     **************************************************

CI   PFQLGLLVVFLATQEVLRKRWTAKISMPAILIALLVLVFGGITYTDVLRY
FLA  PFQLGLLVVFLATQEVLRKRWTAKISMPAILIALLVLVFGGITYTDVLRY
     **************************************************

CI   VILVGAAFAESNSGGDVVHLALMATFKIQPVFMVASFLKARWTNQENILL
FLA  VILVGAAFAESNSGGDVVHLALMATFKIQPVFMVASFLKARWTNQENILL
     **************************************************

CI   MLAAVFFQMAYHDARQILLWEIPDVLNSLAVAWMILRAITFTTTSNVVVP
FLA  MLAAVFFQMAYHDARQILLWEIPDVLNSLAVAWMILRAITFTTTSNVVVP
     **************************************************

CI   LLALLTPRLRCLNLDVYRILLLMVGIGSLIREKRSAAAKKKGASLLCLAL
FLA  LLALLTPGLRCLNLDVYRILLLMVGIGSLIREKRSAAAKKKGASLLCLAL
     ******* ******************************************
                                                      NS2B
CI   ASTGLFNPMILAAGLIACDPNRKRGWPATEVMTAVGLMFAIVGGLAELDI
FLA  ASTGLFNPMILAAGLIACDPNRKRGWPATEVMTAVGLMFAIVGGLAELDI
     **************************************************

CI   DSMAIPMTIAGLMFAAFVISGKSTDMWIERTADISWESDAEITGSSERVD
FLA  DSMAIPMTIAGLMFAAFVISGKSTDMWIERTADISWESDAEITGSSERVD
     **************************************************

CI   VRLDDGENFQLMNDPGAPWKIWMLRMVCLAISAYTPWAILPSVVGFWITL
```

FIG. 1B

```
FLA   VRLDDDGNFQLMNDPGAPWKIWMLRMVCLAISAYTPWAILPSVVGFWITL
      ****.*********************************************
              NS3
CI    QYTKRGGVLWDTPSPKEYKKGDTTTGVYRIMTRGLLGSYQAGAGVMVEGV
FLA   QYTKRGGVLWDTPSPKEYKKGDTTTGVYRIMTRGLLGSYQAGAGVMVEGV
      **************************************************

CI    FHTLWHTTKGAALMSGEGRLDPYWGSVKEDRLCYGGPWKLQHKWNGQDEV
FLA   FHTLWHTTKGAALMSGEGRLDPYWGSVKEDRLCYGGPWKLQHKWNGQDEV
      **************************************************

CI    QMIVVEPGKNVKNVQTKPGVFKTPEGEIGAVTLDFPTGTSGSPIVDKNGD
FLA   QMIVVEPGKNVKNVQTKPGVFKTPEGEIGAVTLDFPTGTSGSPIVDKNGD
      **************************************************

CI    VIGLYGNGVIMPNGSYISAIVQGERMDEPIPAGFEPEMLRKKQITVLDLH
FLA   VIGLYGNGVIMPNGSYISAIVQGERMDEPIPAGFEPEMLRKKQITVLDLH
      **************************************************

CI    PGAGKTRRILPQIIKEAINRRLRTAVLAPTRVVAAEMAEALRGLPIRYQT
FLA   PGAGKTRRILPQIIKEAINRRLRTAVLAPTRVVAAEMAEALRGLPIRYQT
      **************************************************

CI    SAVPREHNGNEIVDVMCHATLTHRLMSPHRVPNYNLFVMDEAHFTDPASI
FLA   SAVPREHNGNEIVDVMCHATLTHRLMSPHRVPNYNLFVMDEAHFTDPASI
      **************************************************

CI    AARGYISTKVELGEAAAIFMTATPPGTSDPFPESNSPISDLQTEIPDRAW
FLA   AARGYISTKVELGEAAAIFMTATPPGTSDPFPESNSPISDLQTEIPDRAW
      **************************************************

CI    NSGYEWITEYTGKTVWFVPSVKMGNEIALCLQRAGKKVVQLNRKSYETEY
FLA   NSGYEWITEYTGKTVWFVPSVKMGNEIALCLQRAGKKVVQLNRKSYETEY
      **************************************************

CI    PKCKNDDWDFVITTDISEMGANFKASRVIDSRKSVKPTIITEGEGRVILG
FLA   PKCKNDDWDFVITTDISEMGANFKASRVIDSRKSVKPTIITEGEGRVILG
      **************************************************

CI    EPSAVTAASAAQRRGRIGRNPSQVGDEYCYGGHTNEDDSNFAHWTEARIM
FLA   EPSAVTAASAAQRRGRIGRNPSQVGDEYCYGGHTNEDDSNFAHWTEARIM
      **************************************************

CI    PDNINMPNGLIAQFYQPEREKVYTMEGEYRLRGEERKNFLELLRTADLPV
FLA   LDNINMPNGLIAQFYQPEREKVYTMDGEYRLRGEERKNFLELLRTADLPV
       ************************ *************************

CI    WLAYKVAAAGVSYHDRRWCFDGPRTNTILEDNNEVEVITKLGERKILRPR
FLA   WLAYKVAAAGVSYHDRRWCFDGPRTNTILEDNNEVEVITKLGERKILRPR
      **************************************************
                                          NS4A
CI    WIDARVYSDHQALKAFKDFASGKRSQIGLIEVLGKMPEHFMGKTWEALDT
FLA   WIDARVYSDHQALKAFKDFASGKRSQIGLIEVLGKMPEHFMGKTWEALDT
      **************************************************

CI    MYVVATAEKGGRAHRMALEELPDALQTIALIALLSVMTMGVFFLLMQRKG
FLA   MYVVATAEKGGRAHRMALEELPDALQTIALIALLSVMTMGVFFLLMQRKG
      **************************************************

CI    IGKIGLGGAVLGVATFFCWMAEVPGTKIAGMLLLSLLLMIVLIPEPEKQR
```

FIG. 1C

```
FLA    IGKIGLGGAVLGVATFFCWMAEVPGTKIAGMLLLSLLLMIVLIPEPEKQR
       *************************************************
                               NS4B
CI     SQTDNQLAVFLICVMTLVSAVAANEMGWLDKTKSDISSLFGQRIEVKENF
FLA    SQTDNQLAVFLICVMTLVSAVAANEMGWLDKTKSDISSLFGQRIEVKENF
       *************************************************

CI     SMGEFLLDLRPATAWSLYAVTTAVLTPLLKHLITSDYINTSLTSINVQAS
FLA    SMGEFLLDLRPATAWSLYAVTTAVLTPLLKHLITSDYINTSLTSINVQAS
       *************************************************

CI     ALFTLARGFPFVDVGVSALLLAAGCWGQVTLTVTVTAATLLFCHYAYMVP
FLA    ALFTLARGFPFVDVGVSALLLAAGCWGQVTLTVTVTAATLLFCHYAYMVP
       *************************************************

CI     GWQAEAMRSAQRRTAAGIMKNAVVDGIVATDVPELERTTPIMQKKVGQIM
FLA    GWQAEAMRSAQRRTAAGIMKNAVVDGIVATDVPELERTTPIMQKKVGQIM
       *************************************************

CI     LILVSLAAVVVNPSVKTVREAGILITAAAVTLWENGASSVWNATTAIGLC
FLA    LILVSLAAVVVNPSVKTVREAGILITAAAVTLWENGASSVWNATTAIGLC
       *************************************************
                             NS5
CI     HIMRGGWLSCLSITWTLIKNMEKPGLKRGGAKGRTLGEVWKERLNQMTKE
FLA    HIMRGGWLSCLSITWTLIKNMEKPGLKRGGAKGRTLGEVWKERLNQMTKE
       *************************************************

CI     EFTRYRKEAIIEVDRSAAKHARKEGNVTGGHSVSRGTAKLRWLVERRFLE
FLA    EFTRYRKEAIIEVDRSAAKHARKEGNVTGGHPVSRGTAKLRWLVERRFLE
       ******************************* *****************

CI     PVGKVIDLGCGRGGWCYYMATQKRVQEVRGYTKGGPGHEEPQLVQSYGWN
FLA    PVGKVIDLGCGRGGWCYYMATQKRVQEVRGYTKGGPGHEEPQLVQSYGWN
       *************************************************

CI     IVTMKSGVDVFYRPSECCDTLLCDIGESSSSAEVEEHRTIRVLEMVEDWL
FLA    IVTMKSGVDVFYRPSECCDTLLCDIGESSSSAEVEEHRTIRVLEMVEDWL
       *************************************************

CI     HRGPREFCVKVLCPYMPKVIEKMELLQRRYGGGLVRNPLSRNSTHEMYWV
FLA    HRGPREFCVKVLCPYMPKVIEKMELLQRRYGGGLVRNPLSRNSTHEMYWV
       *************************************************

CI     SRASGNVVHSVNMTSQVLLGRMEKRTWKGPQYEEDVNLGSGTRAVGKPLL
FLA    SRASGNVVHSVNMTSQVLLGRMEKRTWKGPQYEEDVNLGSGTRAVGKPLL
       *************************************************

CI     NSDTSKINNRIERLRREYSSTWHHDENHPYRTWNYHGSYDVKPTGSASSL
FLA    NSDTSKIKNRIERLRREYSSTWHHDENHPYRTWNYHGSYDVKPTGSASSL
       *******.*****************************************

CI     VNGVVRLLSKPWDTITNVTTMAMTDTTPFGQQRVFKEKVDTKAPEPPEGA
FLA    VNGVVRLLSKPWDTITNVTTMAMTDTTPFGQQRVFKEKVDTKAPEPPEGV
       ************************************************

CI     KYVLNETTNWLWAFLAREKRPRMCSREEFIRKVNSNAALGAMFEEQNQWR
FLA    KYVLNETTNWLWAFLAREKRPRMCSREEFIRKVNSNAALGAMFEEQNQWR
       *************************************************

CI     SAREAVEDPKFWEMVDEEREAHLRGECHTCIYNMMGKREKKPGEFGKAKG
```

FIG. 1D

```
FLA      SAREAVEDPKFWEMVDEEREAHLRGECHTCIYNMMGKREKKPGEFGKAKG
         **************************************************

CI       SRAIWFMWLGARFLEFEALGFLNEDHWLGRKNSGGGVEGLGLQKLGYILR
FLA      SRAIWFMWLGARFLEFEALGFLNEDHWLGRKNSGGGVEGLGLQKLGYILR
         **************************************************

CI       EVGTRPGGKIYADDTAGWDTRITRADLENEAKVLELLDGEHRRLARAIIE
FLA      EVGTRPGGKIYADDTAGWDTRITRADLENEAKVLELLDGEHRRLARAIIE
         **************************************************

CI       LTYRHKVVKVMRPAADGRTVMDVISREDQRGSGQVVTYALNTFTNLAVQL
FLA      LTYRHKVVKVMRPAADGRTVMDVISREDQRGSGQVVTYALNTFTNLAVQL
         **************************************************

CI       VRMMEGEGVIGPDDVEKLTKGKGPKVRTWLFENGEERLSRMAVSGDDCVV
FLA      VRMMEGEGVIGPDDVEKLTKGKGPKVRTWLFENGEERLSRMAVSGDDCVV
         **************************************************

CI       KPLDDRFATSLHFLNAMSKVRKDIQEWKPSTGWYDWQQVPFCSNHFTELI
FLA      KPLDDRFATSLHFLNAMSKVRKDIQEWKPSTGWYDWQQVPFCSNHFTELI
         **************************************************

CI       MKDGRTLVVPCRGQDELVGRARISPGAGWNVRDTACLAKSYAQMWLLLYF
FLA      MKDGRTLVVPCRGQDELVGRARISPGAGWNVRDTACLAKSYAQMWLLLYF
         **************************************************

CI       HRRDLRLMANAICSAVPVNWVPTGRTTWSIHAGGEWMTTEDMLEVWNRVW
FLA      HRRDLRLMANAICSAVPVNWVPTGRTTWSIHAGGEWMTTEDMLEVWNRVW
         **************************************************

CI       IEENEWMEDKTPVEKWSDVPYSGKREDIWCGSLIGTRARATWAENIQVAI
FLA      IEENEWMEDKTPVEKWSDVPYSGKREDIWCGSLIGTRARATWAENIQVAI
         **************************************************

CI       NQVRAIIGDEKYVDYMSSLKRYEDTTLVEDTVL
FLA      NQVRAIIGDEKYVDYMSSLKRYEDTTLVEDTVL
         *********************************
```

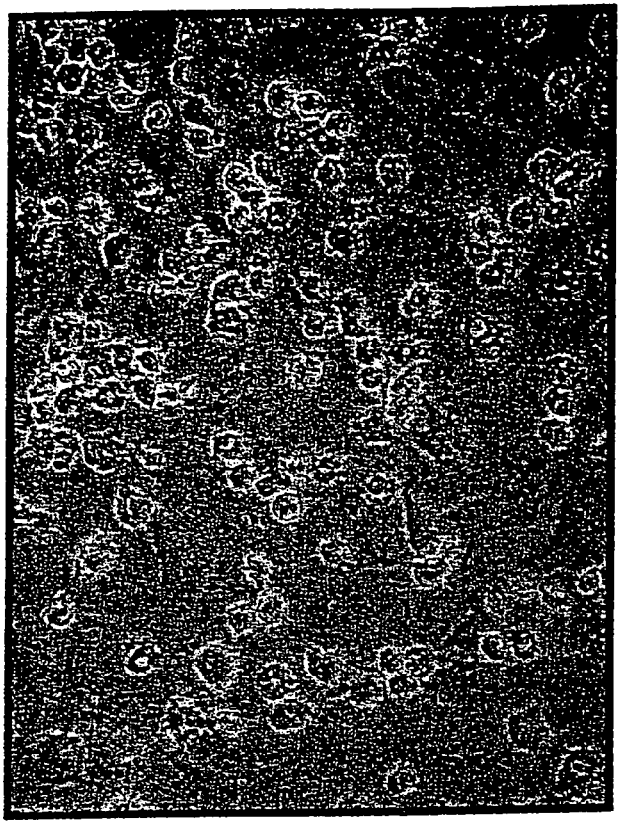
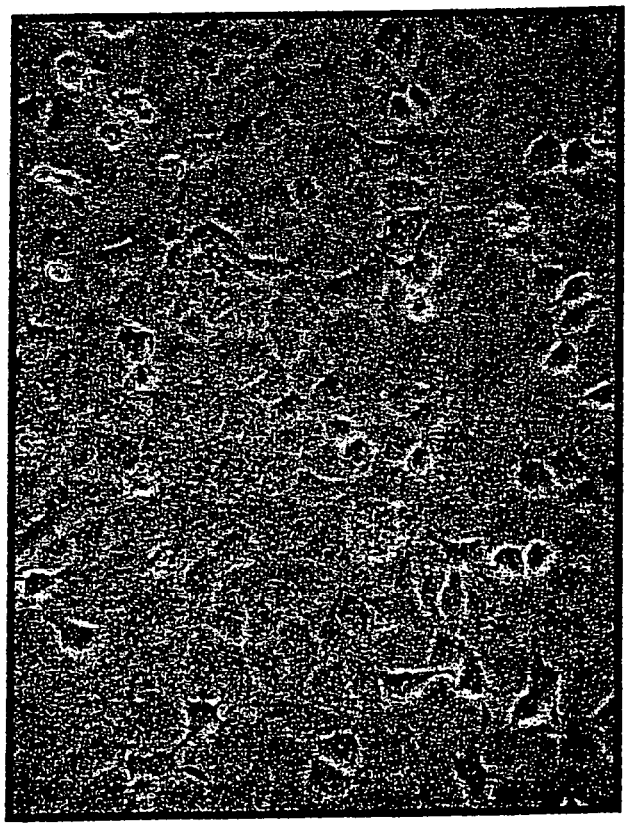
Strain IS-98-ST1 (m.i. of 4) 24 h of infection
Control
FIG. 5

Mice

Inbred laboratory mice:

BALB/c, C57BL/6, DDK, 129, C3H and DBA/1
→ sensitive to infection with the WN virus Wild mice:

SEG/Pas (*Mus spretus*), MAI/Pas, MBT/Pas (*Mus m. musculus*)
→ resistant to infection with the WN virus Generation of first backcross (BC1) mice

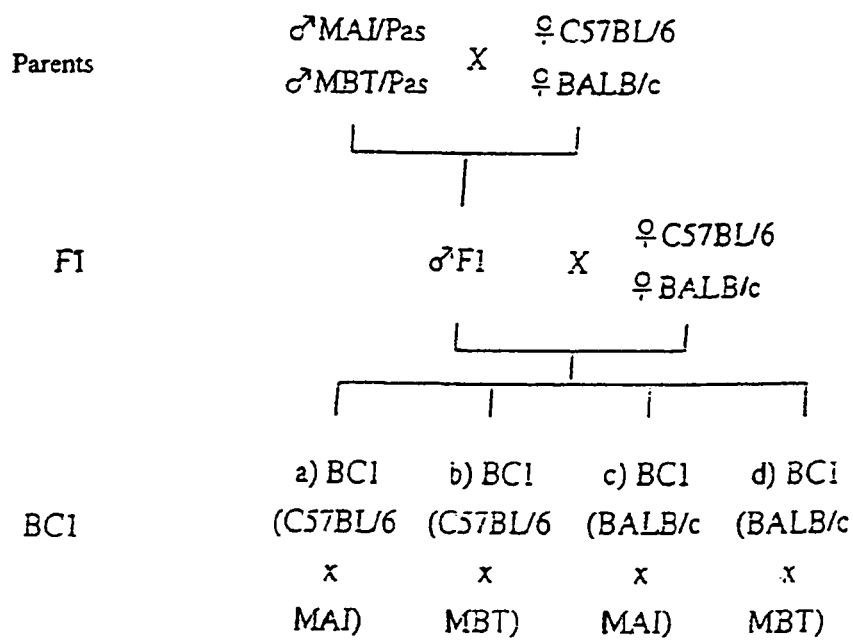

Virus

Injection of West Nile (WN) virus 5-week-old mice

Observation of mice for 14 days following infection

**Genotyping of *Flv* alleles** markers flanking the *Flv* locus on m

| $Flv^*$ Phenotype | Survivors | Deaths | Total |
|---|---|---|---|
| Resistant ($Flv^r/Flv^s$) | 108 | 0 | 108 (55%) |
| Sensitive ($Flv^s/Flv^s$) | 21 | 74 | 95 (45%) |
| Total | 129 (66%) | 74 (34%) | 203 |

* one $Flv^r$ allele is sufficient to confer resistance

*FIG. 10*

NEUROVIRULENT STRAIN OF THE WEST NILE VIRUS AND USES THEREOF

CROSS-REFERENCE TO RELATED APPLICATIONS

This application is a Continuation Application of Ser. No. 10/474,186, filed Oct. 6, 2003 abandoned, which is a National Stage Application of PCT/FR02/01168 filed Apr. 4, 2002.

The present invention relates to a neuroinvasive and neurovirulent strain of the West Nile virus, named IS-98-ST1, to nucleic acid molecules derived from its genome, to the proteins and peptides encoded by said nucleic acid molecules and to uses thereof.

The present invention also relates to all variants of the viral strain IS-98-ST1 which have at least one mutation in the nucleic acid sequence corresponding to NS5.

The family Flaviviridae includes the viruses of the flavivirus genus which are responsible for serious human pathological conditions such as dengue, yellow fever, tick-borne encephalitis, Japanese encephalitis or West Nile encephalitis and the hepatitis C and G viruses. While flaviviruses are capable of causing considerable morbidity and mortality in humans, the infection is generally asymptomatic and only a fraction of the individuals infected develop a serious disease.

Flaviviruses are small enveloped viruses. Their genome is a single-stranded RNA molecule of positive polarity, approximately 11 000 bases in length. The genomic RNA is associated with several copies of capsid protein C, so as to form the nucleocapsid; it is surrounded by a viral envelope consisting of a double lipid layer derived from the membranes of the endoplasmic reticulum (ER), in which the envelope protein E and the membrane protein M are anchored. The genomic RNA of flaviviruses contains a single open reading frame of approximately 10 500 nucleotides flanked by two short non-coding regions at its 5' and 3' ends. The genome is translated into a polyprotein of approximately 3 400 amino acids which is the precursor of the structural proteins C, prM (intracellular precursor of M) and E in its N-terminal portion, and of at least seven nonstructural (NS) proteins, from NS1 to NS5, in its C-terminal portion.

Until very recently, the West Nile virus was recognized as being a relatively nonpathogenic virus responsible for a flu-like syndrome and present in Africa, in southern Europe and in the Middle East; it was isolated during epidemics which occurred, in particular, in Israel in the 1950s and in South Africa in the 1970s.

Very recently, the epidemiology of the West Nile virus became modified and an increasing number of cases of encephalitis was observed during the epidemics occurring in Romania in 1996, in Israel in 1998 and in the USA in 1999. Pathogenic strains were isolated during these epidemics (Anderson et al., and Lanciotti et al., Science, 1999, 286: 2331-2333, 2333-2337), in particular the strain NY1999 (GenBank No. AF202541, Lanciotti et al., mentioned above), the pathogenicity of which is thought to be correlated with the presence of an NTS glycosylation site in the envelope protein E (Jordan et al., Viral Immunol., 2000, 13, 4: 435-446).

All the poorly identified viral factors may be responsible for the seriousness of the infection, whereas the genetic constitution of the host (human or nonhuman) is thought to contribute to resistance to infection.

However, the data relating to these recently isolated pathogenic strains have not made it possible to determine all the viral factors and host genes involved in sensitivity/resistance to infection with Flaviviridae.

Murine models have made it possible to establish the existence of genetic resistance to infection with flaviviruses. It has been shown that certain mouse lines recently derived from the wild and belonging to the species *Mus musculus* musculus or *Mus spretus* (Det, BSVR, BRVR, PRI, CASA/Rk and CAST/Ei) are resistant to infection with flaviviruses, whereas the most common inbred laboratory lines, which derive mainly from the species *Mus musculus* domesticus, are not resistant to it (Sangster et al., J. Virol., 1993, 67: 340-347).

Resistance is controlled by at least one autosomal locus named Flv, located on chromosome 5, in mice, and three alleles, $Flv^s$, $Flv^r$ and $Flv^{mr}$, confer, respectively, sensitivity, resistance and intermediate resistance to infection with flaviviruses. Using a Murray valley encephalitis flavivirus strain and mice derived from backcrossing the resistant mouse line C3H/RV with the sensitive mouse line C3/He or BALB/c, the Flv locus was located in a 0.9 cM region of chromosome 5, in mice, between the markers D5Mit68 and D5Mit242 (G. R. Shellam et al., Rev. Sci. Tech. Off. Epiz. 1998, 17: 231-248).

The inventors have now isolated a novel strain of the West Nile virus, from samples taken from storks in Israel (in the town of Eilat) in September 1998, which was selected for studying the resistance/sensitivity of a host (human or non-human mammal) to infection with viruses of the family Flaviviridae.

In accordance with the invention, said isolated neurovirulent and neuroinvasive strain of the West Nile virus, named IS-98-ST1, is characterized in that its genome consists of the sequence SEQ ID No. 1 which encodes a polyprotein having the sequence SEQ ID No. 2.

The inventors have in particular shown that laboratory mice are extremely sensitive to infection with the strain IS-98-ST1, whereas the mouse lines SEG, WMP, STF and MAI, which derive from wild mice belonging to species which are different although of the same genus *Mus*, are completely resistant to infection with this strain; an intraperitoneal inoculation of 1 000 FFU (focus-forming units; FFU: LD50=100) is 100% lethal for laboratory mice, whereas the wild mice do not show any symptoms; in addition, the virus replicates in these mice, as shown by the appearance of specific serum antibodies.

A subject of the present invention is also reagents, derived from the strain IS-98-ST1, used for studying and diagnosing infections with Flaviviridae, which reagents are selected from the group consisting of the following reagents:

(a) a nucleic acid molecule chosen from the sequence SEQ ID No. 1, the fragments of at least 15 nucleotides of the sequence SEQ ID No. 1 and the sense and antisense sequences complementary to the above sequences, excluding the fragment having the GENBANK sequence AF205882.

(b) a recombinant vector comprising a nucleic acid molecule as defined in (a), (c) a cell transformed with a nucleic acid molecule as defined in (a), a vector as defined in (b) or a neurovirulent strain of the West Nile virus as defined in (a), (d) a protein or a peptide encoded by a nucleic acid molecule as defined in (a), (e) a polyclonal antibody which can be obtained by immunizing a nonhuman mammal with the strain IS-98-ST1 of the West Nile virus, as defined above; preferably, said nonhuman mammal is a mouse homozygous for the $Flv^r$ allele, resistant to infection with Flaviviridae, and (f) a polyclonal or monoclonal antibody which can be obtained by immunizing a nonhuman mammal with a recombinant vector as defined in (b) or a protein or a peptide as defined in (d).

These various reagents are prepared and used according to the conventional techniques of molecular biology and immunology, according to standard protocols such as those described in *Current Protocols in Molcular Biology* (Frederick M. AUSUBEL, 2000, Wiley and Son Inc. Library of Congress, USA) and in *Current Protocols in Immunology* (John E. Coligan, 2000, Wiley and Son Inc. Library of Congress, USA).

The nucleic acid fragments as defined above, in particular those corresponding to the sequences SEQ ID Nos. 3-11, are used, for example, as a probe or as a primer for diagnosing infection with the West Nile virus; the infection is detected, for example, by PCR and/or hybridization, using the nucleic acids extracted from a biological sample taken from an individual liable to be infected or a laboratory animal inoculated with said virus.

According to an advantageous embodiment of said fragments, they comprise at least 15 nucleotides of SED ID No. 1, upstream or downstream of one of the codons at the following position:

alanine (A) codon at positions 1117-1119, corresponding to the residue at position 51 of the E protein or at position 341 of the sequence of the viral polyprotein of sequence SEQ ID No. 2 (the sequence of the E protein extends from the codons at position 291 to 791 of the sequence SEQ ID No. 2, corresponding to nucleotides 967 to 2469 of the sequence SEQ ID No. 1), asparagine (N) codon at positions 2518-2520, corresponding to the residue at position 17 of the NS1 protein or at position 808 of the sequence SEQ ID No. 2 (the sequence of the NS1 protein extends from the codons at position 792 to 1144 of the sequence SEQ ID No. 2, corresponding to nucleotides 2470 to 3528 of the sequence SEQ ID No. 1), arginine (R) codon at positions 4018-4020, corresponding to the residue at position 164 of the NS2A protein or at position 1308 of the sequence SEQ ID No. 2 (the sequence of the NS2A protein extends from the codons at position 1145 to 1374 of the sequence SEQ ID No. 2, corresponding to nucleotides 3529 to 4218 of the sequence SEQ ID No. 1), glycine (G) codon at positions 4462-4464 and glutamic acid (E) codon at positions 4465-4467, corresponding, respectively, to the residue at position 82 and 83 of the NS2B protein or at position 1456 and 1457 of the sequence SEQ ID No. 2 (the sequence of the NS2B protein extends from the codons at position 1375 to 1505 of the sequence SEQ ID No. 2, corresponding to nucleotides 4219 to 4611 of the sequence SEQ ID No. 1), proline (P) codon at positions 6097-6099 and glutamic acid codon at positions 6172-6174, corresponding, respectively, to the residue at position 496 and 521 of the NS3 protein or at position 2001 and 2026 of the sequence SEQ ID No. 2 (the sequence of the NS3 protein extends from the codons at position 1506 to 2124 of the sequence SEQ ID No. 2, corresponding to nucleotides 4612 to 6468 of the sequence SEQ ID No. 1), and serine (S) codon at positions 7840-7842, asparagine (N) codon at positions 8518-8520 and alanine (A) codon at positions 8794-8796, corresponding, respectively, to the residue at position 54, 280 and 372 of NS5 or at position 2582, 2808 and 2900 of the sequence SEQ ID No. 2 (the sequence of the NS5 protein extends from the codons at position 2529 to 3430 of the sequence SEQ ID No. 2, corresponding to nucleotides 7681 to 10386 of the sequence SEQ ID No. 1).

Such primers are useful for amplifying fragments containing said codons.

Said primers are preferably located between 10 and 100 nucleotides upstream or downstream of said codons.

According to another advantageous embodiment of said fragments, they consist of the fragments comprising the abovementioned codons, preferably of between 50 and 200 nucleotides, which are amplified using the primers as defined above.

The recombinant vectors as defined above, in particular the expression vectors, and the cells transformed with said expression vectors, are advantageously used for producing the corresponding peptides and proteins.

Said proteins and said peptides, which can be recognized by, and/or can induce the production of, antibodies specific for the West Nile virus, in particular for neurovirulent strains, are useful for diagnosing infection with a West Nile virus; the infection is detected using a suitable technique, in particular EIA, ELISA, RIA or immunofluorescence, using a biological sample taken from an individual liable to be infected or a laboratory animal inoculated with said virus. The proteins and peptides as defined above are also used to investigate cellular partners of these viral proteins which may be involved in the pathogenicity (neurovirulence) of the West Nile virus; these partners are identified using immunoaffinity techniques, for example using immunoaffinity column chromatography.

The antibodies according to the invention are useful for diagnosing infection with a West Nile virus, in particular neurovirulent strains; the infection is detected using a suitable technique, in particular EIA, ELISA, RIA or immunofluorescence, using a biological sample taken from an individual liable to be infected or a laboratory animal inoculated with said virus. Among these antibodies, those produced by immunizing $Flv^r/Flv^r$ mice with the strain IS-98-ST1 advantageously have a high titer and a very high specificity for the West Nile virus.

The transformed cells according to the invention, in particular neural cells (neurons and endothelial cells) infected with a neurovirulent strain as defined above, are used to identify the genes derived from these cells, the expression of which may be modulated during the viral infection; these genes are detected, for example, using biochip technology according to conventional protocols as described in Atlas Mouse Arrays (#membranes) ATLAS™ NYLON cDNA EXPRESSION ARRAYS (CLONTECH, USA).

A subject of the present invention is also a model for studying sensitivity/resistance to infection with a virus of the family Flaviviridae, characterized in that it comprises at least one neurovirulent strain of the West Nile virus as defined above.

According to an advantageous embodiment of said model, it also comprises a mouse homozygous for the $Flv^r$ or $Flv^s$ allele.

A subject of the present invention is also a method for detecting Flaviviridae infection, in particular a West Nile virus infection, characterized in that it comprises:

amplifying the RNAs derived from a biological sample to be tested, using the primers as defined above, and sequencing the amplification product obtained.

Such a detection may advantageously make it possible to establish a prognosis for the severity of a viral encephalitis caused by the West Nile virus.

The neurovirulent strain of the West Nile virus according to the invention is used to screen cellular genes involved in the resistance of a mammal to infection with a virus of the family Flaviviridae, preferably the hepatitis C virus.

Advantageously, said screening method comprises the following steps:
- culturing cells derived from a host (human or nonhuman) selected for its resistance or its sensitivity to infection with a Flaviviridae,
- infecting said cells with a Flaviviridae, in vitro, and
- detecting genes expressed differentially in said infected cells.

In accordance with the invention, said detection may comprise establishing the transcript or protein profile using said cells.

A subject of the present invention is also the use of the model as defined above for sorting molecules which are active against a viral infection due to a virus of the family Flaviviridae.

A subject of the present invention is also a method for sorting molecules which are active against infection with a Flavivirus, characterized by:
- bringing a culture of eukaryotic cells, derived from a mammal (human or nonhuman) sensitive to infection with a Flaviviridae, into contact with a viral suspension of the strain as claimed in claim 1, in the presence or absence of the molecule to be tested, and
- detecting the amplification/replication of the virus, by any known method (quantification genome, mRNA, proteins, viral particles).

A subject of the present invention is also a variant of the viral strain as defined above, characterized in that its genome comprises at least one mutation in the nucleotide sequence corresponding to the NS5 protein.

Figure 7:
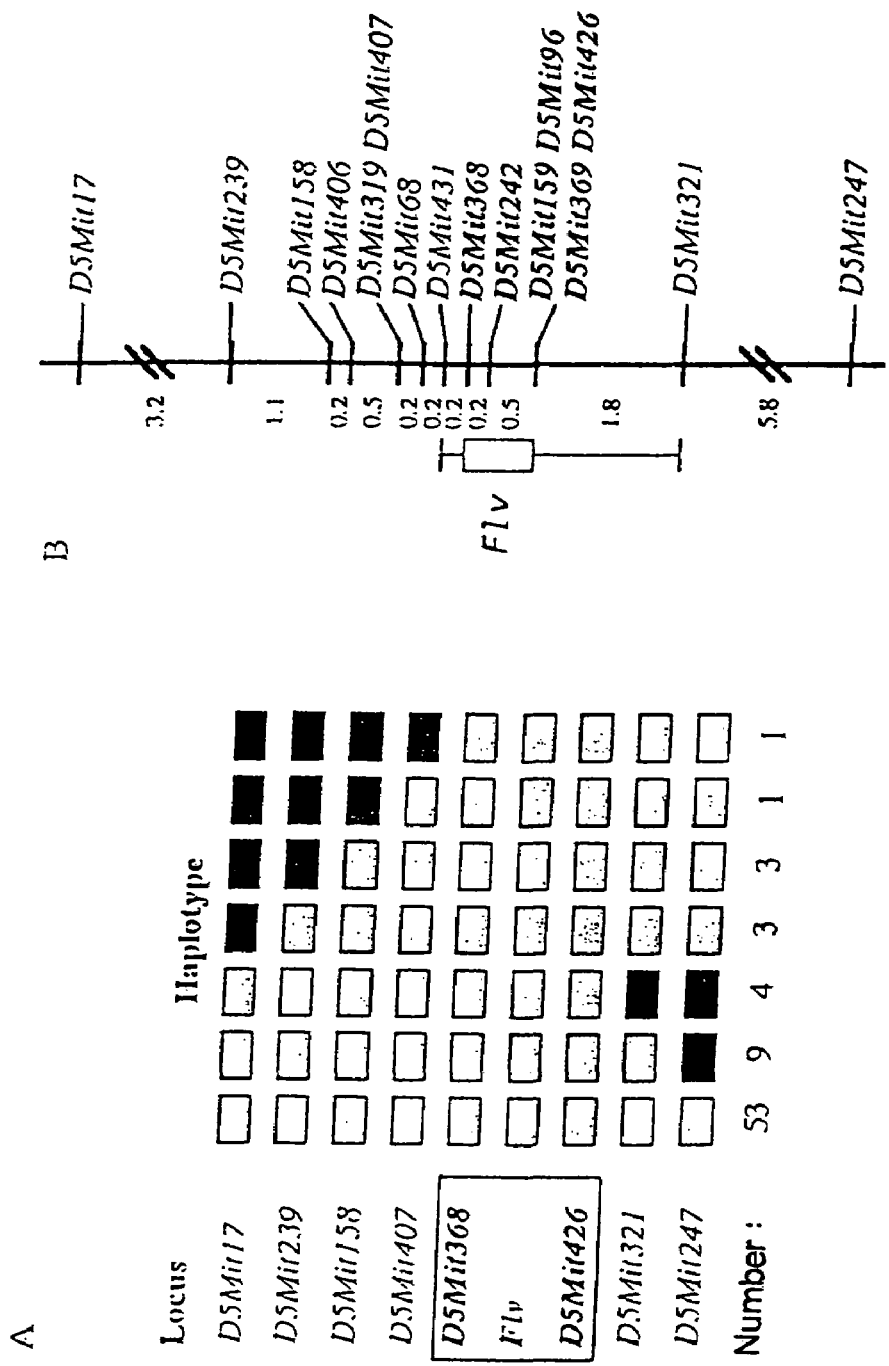
Figure 8:
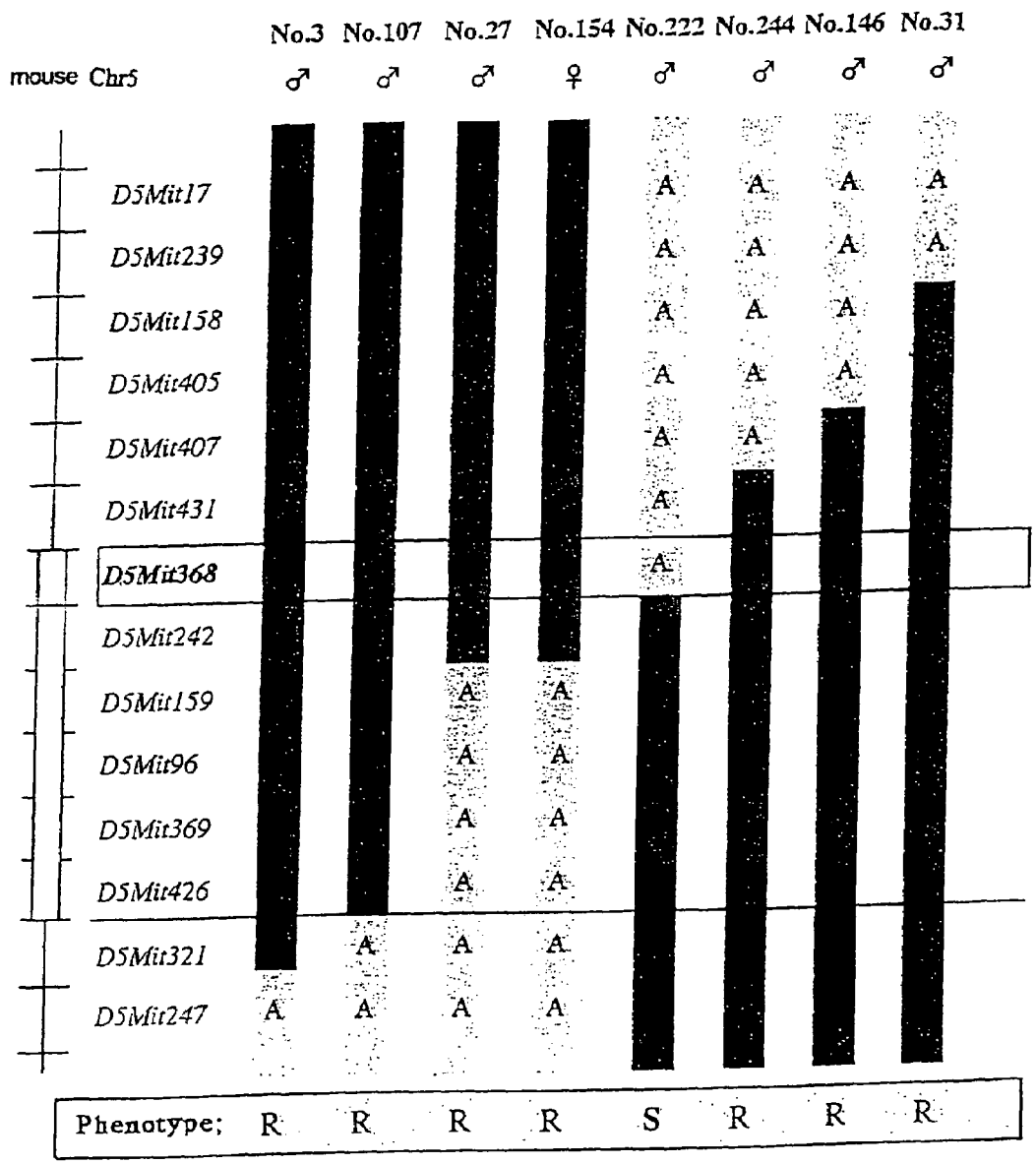

Besides the above arrangements, the invention also comprises other arrangements which will emerge from the following description, which refers to examples of implementation of the subject of the present invention, with references to the attached drawings in which:

FIGS. 1A to 1E represent the comparison of the amino acid sequence of the viral proteins of the strain IS-98-ST1 (SEQ ID No. 2), isolated from storks (CI), and of the New York strain (NY99; Genbank AF196835-SEQ ID NO:12) isolated from pink flamingos during the 1999 epidemic in the United States, FIG. 2 represents the kinetics of mortality and the kinetics of appearance of specific serum antibodies in Flv$^s$/Flv$^s$ sensitive mice (BALB/c) infected with the IS-98-ST1 strain of the West Nile virus, FIG. 3 represents the kinetics of propagation of the strain IS-98-ST1 in the central nervous system of Flv$^s$/Flv$^s$ sensitive mice (BALB/c), FIGS. 4 (A, B and C) represent the kinetics of appearance of the viral antigens in Neuro 2a cells and primary neurons from sensitive mice (BALB/c) infected with the West Nile virus (strain IS-98-ST1), FIG. 5 represents the death by necrosis of Neuro 2a cells infected with the West Nile virus (strain IS-98-ST1), FIG. 6 represents the experimental protocol used to specify the location of the Flv locus on mouse chromosome 5, FIG. 7 represents the genetic map of the Flv locus, determined using sensitive mice derived from the first backcross between resistant lines (MAI/Pas and MBT/Pas) and sensitive lines (C57BL/6 or BALB/c). The white boxes represent the BALB/c or C57Bl/6 alleles and the black boxes represent the MAI/Pas or MBT/Pas alleles, FIG. 8 represents the genetic map of the Flv locus, determined using resistant mice and sensitive mice, derived from the first backcross (BC1) between resistant lines (MAI/Pas and MBT/Pas) and sensitive lines (C57BL/6 and BALB/c). The shaded lines represent the BALB/c or C57Bl/6 alleles and the black lines represent the MAI/Pas or MBT/Pas alleles.

Figure 9:
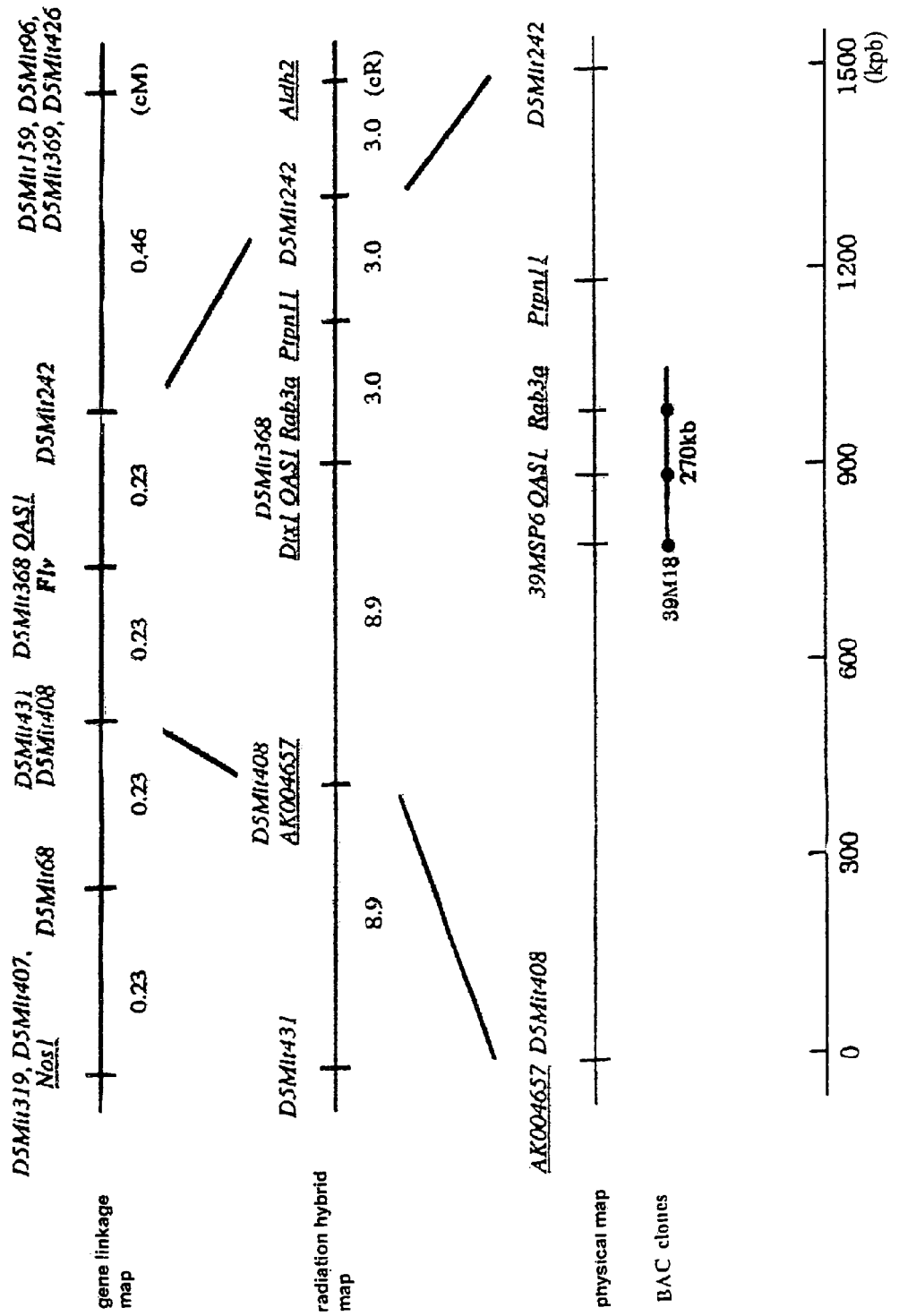

FIG. 9 represents the genetic map and the physical map of the Flv locus and the position of the OAS gene in this locus, and FIG. 10 represents the distribution of Flv alleles in resistant mice and sensitive mice, derived from the first backcross (BC1) between resistant lines (MAI/Pas and MBT/Pas) and sensitive lines (C57BL/6 and BALB/c).

EXAMPLE 1

Isolating, Amplifying, Purifying and Titering the Neuroinvasive Strain of the West Nile Virus, IS-98-ST1

An isolate of the West Nile (WN) virus was obtained from the central nervous system of a stork exhibiting severe neuropathological problems, in September 1998 in Eilat (Israel). Infection of VERO cells with this isolate is cytolytic and indirect immunofluorescence with an immune mouse ascites specific for the West Nile virus (immune serum of reference WN 8907) is 100% positive. The virus produced on VERO cells was harvested and amplified on AP61 mosquito cells (Després et al., Virol., 1993, 196, 209-219).

Passage 1 (or P1) of the WN virus on AP61 cells was harvested 3 days after infection; it has a titer of $2.5 \times 10^8$ FFU/ml (Focus-Forming Unit) by the technique for titering on AP61 cells described in Després et al. (mentioned above). The P1 inoculum of the WN virus on AP61 cells was identified as the strain IS-98-ST1.

A P2 was obtained from AP61 cells infected with the strain IS-98-ST1, P1 (titer: $6 \times 10^7$ FFU/ml). The P2 inoculum of IS-98-ST1 is used for the tests for sensitivity to viral infection in adult mice.

A P3 viral inoculum of the strain IS-98-ST1, with a titer of $5 \times 10^7$ FFU/ml, was produced on PA61 cells. A highly purified viral preparation, prepared according to the flavivirion purification protocol described in Després et al., 1993) was obtained from twenty 150 cm$^2$ dishes of AP61 cells harvested 3 days after infection with the P3 inoculum of the WN virus strain IS-98-ST1 (multiplicity of infection of 0.4). The strain IS-98-ST1 purified on sucrose gradients has a final titer of $2 \times 10^{10}$ FFU/ml. The RNAs extracted from this purified virus are used to amplify the cDNAs corresponding to the C, prM and NS1 viral proteins or to the noncoding sequences at the 5' and 3' ends of the viral genome.

EXAMPLE 2

Sequencing the Genome of the Neuroinvasive Strain IS-98-ST1

The viral genome was extracted from the culture supernatant of the infected VERO cells of example 1 using the "QIAamp Viral RNA" kit (QUIAGEN), according to the manufacturer's instructions. 6 overlapping RT-PCR products were amplified from these RNAs using the primers described by Lanciotti et al. (mentioned above). The 5' and 3' ends of the viral genome were amplified, respectively, using the following primers:

5'AGTAGTTCGCCTGTGTGAGCTGACAAAC 3',   (SEQ ID No. 5)
and
5'AGATCCTGTGTTCTCGCACCACCAGCCAC 3'.   (SEQ ID No. 6)

The cDNA corresponding to the E viral protein was amplified using the primers 5'GGATGGATGCT(A/T)GG(G/T)AGCAAC 3' (SEQ ID No. 7) and 5'CCATCCAAGCCTCCACATC 3' (SEQ ID No. 8), which hybridize, respectively, in the gene of the M protein (positions 889 to 909 of the sequence SEQ ID No. 1) and in the gene of the NS1 protein (positions 2539 to 2557 of the sequence SEQ ID No. 1).

The cDNAs obtained were purified by ion exchange chromatography and precipitated in 2 volumes of isopropanol. The cDNAs were then sequenced on both strands using the "Taq Dye Deoxy Terminator Cycle Sequencing" kit (PERKIN ELMER CORP./APPLIED BIOSYSTEM) and primers 400 base pairs apart on the viral genome (Lanciotti et al., mentioned above). The sequencing was performed with 0.2 pmol of purified cDNA and 30 pmol of primers, according to the protocol recommended by the manufacturer. The sequence alignment is produced using the CLUSTAL W program.

The complete genomic sequence of the strain IS-98-ST1 of the West Nile virus corresponds to the sequence SEQ ID No. 1.

The amino acid sequence alignment for the strain IS-98-ST1 (SEQ ID No. 2) and the strain NY99, given in FIG. 1, shows that the strain IS-98-ST1 isolated in Israel in 1998 and the strain NY-99 isolated in New York in 1999 are very close (less than 0.2% divergence at the amino acid sequence level).

However, the differences observed in the strain IS-98-ST1 in the E ($A_{51}$), NS1 ($N_{17}$), NS2A ($R_{164}$), NS2B ($G_{82}$, $E_{83}$), NS3 ($P_{496}$, $E_{521}$) and NS5 ($S_{54}$, $N_{280}$, $A_{372}$) proteins, respectively, are potentially responsible for the neurovirulence and for the neuroinvasive properties observed with this strain and may be used as a virulence marker for the West Nile virus.

EXAMPLE 3

Cloning the Proteins of the Neuroinvasive Strain IS-98-ST1 and Uses of the Recombinant Plasmids Obtained 1—The C Protein The genomic RNA extracted from the IS-98-ST1 virions purified on sucrose gradients described in example 1, using the RNA PLUS 2 solution (Q.BIOGEN), is used as a matrix for amplifying the sequence encoding the C protein (amino acids 1 to 123) using the RT-PCR technique (Titan One Tube RT-PCR kit; Roche Biochemicals #1939 823).

The pair of primers used on the RNA matrix is as follows:
5'C/WNV (sequence of nt 81-117 of the sequence SEQ ID No. 1) 5'TAGCACGAAGAATTCGATGTCTAAAAACCAGGAGGG 3' (SEQ ID No. 11), which contains the EcoRI restriction site, and 3'C/WNV (antisense sequence of nt 433 to 482 of the sequence SEQ ID No. 1) 5'AAGTTAGCCCGGGTTAATGCTCCTACGCTGGCGATCAGGCCAATCAGGAC 3' (SEQ ID No. 4), which contains the SmaI restriction site.

The cDNA of the C protein of the strain IS-98-ST1 (amino acids 1 to 123) of the WN virus was cloned, firstly, between the EcoRI and SmaI sites of the plasmid pCI-neo (Promega #E1841) and, secondly, between the KspI and SmaI sites of the plasmid PIVEX 2.4a (Roche).

The recombined plasmid pCI-C/WN (registered on Jun. 21, 2001, with the Collection Nationale de Culture de microorganismes [National Collection of Microorganism Cultures] of the Pasteur Institute in Paris, 28, rue du Docteur Roux, 75724, PARIS Cedex 15, under the number I-2688) contains the complete sequence of the C protein gene of the strain IS-98-ST1 of the WN virus, between the T7 and T3 promoters. The transcription, in vitro, of pCI-C/WN linearized with NheI, under the control of the T3 promoter, synthesizes an RNA of approximately 350 bases complementary to the genomic viral sequence. The riboprobe labeled with DIG (digoxigenin) is used to detect the positive-sense viral RNAs in cells infected with the WN virus, using the in situ hybridization technique, according to the protocol described in Després et al., (*J. Virol.*, 1998, 72: 823-829).

The recombinant plasmid pIVEX-C/WN is used for the mass production of the WN virus C protein (amino acids 1 to 123) in bacterial lysate (Roche RTS 500 system). The recombinant C protein produced in vitro has, at its N-terminal end, a $[His]_6$ sequence and the cleavage site recognized by the Xa protease, so as, firstly, to allow it to be purified on an Ni column and, secondly, to allow the histidine residues to be removed. The C protein of the strain IS-98-ST1 of the WN virus thus produced is used for structural studies, to search for cellular partners for this protein on an immunoaffinity column, and to produce monospecific antibodies in rabbits.

2—The M Protein

The cDNAs, of the strain IS-98-ST1 of the WN virus, encoding the M protein (amino acids 215 to 290 of the viral polyprotein) or its 41 amino acid ectodomain (amino acids 215 to 255; acronym ectoM) are cloned:

(1) in phase with the C-terminal end of EGFP, into the plasmid p[95-114]EGFP, derived from the plasmid PEGFP-N1 (Clontech), which comprises residues 95-114 of the C protein of dengue virus type 1 (strain BR/90), fused in phase with the N-terminal sequence of the protein EGFP[215-290] WNV, to give the plasmid p[95-114]EGFP[215-290] WNV, (2) into the plasmid pIVEX (Roche RTS 500 system), to give the plasmid pIVEX[EGFP][215-255]WNV, (3) into the retroviral vector TRIPdeltaU3CMV, to give the plasmid TRIPdeltaU3CMV[95-114]EGFP[215-255]WNV.

The plasmid pIVEX[EGFP][215-255]WNV allows the extracellular synthesis and the purification of the chimeric protein EGFP-ectoM WNV, which is used, firstly, to produce monospecific antibodies directed against the M protein of the WN virus and, secondly, to search for cellular partners of the ectoM WNV molecule on an immunoaffinity column.

The plasmid TRIPdeltaU3CMV[95-114]EGFP[215-255] WNV is cotransfected into 293T cells with the plasmids 8.7 and G-VSV, in order to produce the viral particles pseudotyped with the G envelope of the vesicular stomatitis virus (VSV), containing the inner proteins of the acquired immunodeficiency virus (HIV) and chimeric CMV[95-114]EGFP [215-255]WNV RNA molecules. Infection of target cells with the nonreplicative recombined vector allows integration of the CMV[95-114]EGFP[(215-255]WNV DNA into the cellular genome and stable expression of the ectodomain of the M-WN protein under the control of the CMV promoter.

3—The NS1 Protein

The genomic RNA extracted from the purified IS-98-ST1 virions is amplified using the RT-PCR technique (Titan One Tube RT-PCR kit; Roche Biochemicals #1939 823) using the following pair of primers:

5'TGGATGGGATCCAATATGCGTGATAGGTCC 3' (SEQ ID No. 9), which contains the BamH1 restriction site, and 3'AAAAGGGTCAATGGTACCAGCATTTTAAGCATTCACGTT 3' (SEQ ID No. 10), which contains the Kpn1 restriction site.

The cDNA encoding the NS1 glycoprotein with its signal peptide (amino acids 767 to 1143 of the viral polyprotein) is cloned between the BamH1 and KpnI sites of the retroviral vector TRIPdeltaU3, so as to produce the recombined plasmid TRIPdeltaU3-CMV-NS1-WN (registered on Jan. 9, 2002, with the Collection Nationale de Culture de Microorganismes [National Collection of Microorganism Cultures] of the Pasteur Institute in Paris, 28 rue du Docteur ROUX, 75724, PARIS Cedex 15, under the number I-2770). The plasmid TRIPdeltaU3-CMV-NS1-WN is cotransfected into 293T cells with the plasmids 8.7 and G-VSV, in order to produce viral particles pseudotyped with the G envelope of the vesicular stomatitis virus (VSV), containing the inner proteins of the acquired immunodeficiency virus (HIV) and chimeric CMV-NS1-WN RNA molecules. Infection of target cells with the nonreplicative recombined vector allows integration of the CMV-NS1-WN DNA into the cellular genome and stable expression of the NS1 protein of the WN virus under the control of the CMV promoter. The NS1 protein of the strain IS-98-ST1 of the WN virus thus produced is used for structural studies, to search for cellular partners of this protein on an immunoaffinity column, and to produce monospecific antibodies in rabbits.

EXAMPLE 4

Wild Mice and Inbred Laboratory Mice Differ in their Sensitivity to Infection with the Neuroinvasive Strain IS-98-ST1 of the West Nile Virus 1—Sensitive Mouse Lines and Cells a) Sensitive Mouse Lines 6-week-old mice from $Flv^s$ sensitive inbred lines (BALB/c) are inoculated intraperitoneally with 100 FFU of the strain IS-98-ST1 of the West Nile virus (FFU:LD50=10), prepared as described in example 1.

100% of these mice die with a mean mortality time of 9±2 days (FIG. 2).

The kinetics of propagation of the strain IS-98-ST1 in the central nervous system of the sensitive mice (BALB/c) was analyzed using brain extracts from the infected mice titered on AP61 cells, according to the technique described in according to the technique described in Després et al. (J. Virol., 1998, 72, 823-829). The results show that the virusis detected in the murine central nervous system (CNS) on the 5th day of infection and viral production is at a maximum on the 7th day (FIG. 3). On the 9th day of infection, the virus is no longer detected in the murine CNS (FIG. 3).

Replication of the WN virus in the CNS and the peripheral organs of the mice infected with the strain IS-98-ST1 is also detected by immunohistology, according to conventional protocols as described in Després et al., 1998 (mentioned above) and by in situ hybridization, according to the protocols described in example 3.

The serum antibodies specifically directed against the proteins of the WN virus are titered by ELISA according to the protocol described in Després et al., 1993 (mentioned above), using the strain IS-98-ST1 purified on a sucrose gradient as described in example 1, as antigen. The results show that the serum antibodies appear on the 5th day of infection and are significantly detected on the 7th day (FIG. 2).

b) Sensitive Cells b1) Primary Cultures

Primary neurons and astrocytes from the CNS of sensitive mice homozygous for the $Flv^s$ allele (Swiss mice, Janvier) are prepared according to conventional protocols. The cells are infected with the strain IS-98-ST1 at a multiplicity of infection of 20 FFU per cell (m.i. of 20). The cytopathic effect is observed by light microscopy, viral production is analyzed by titering on AP61 cells as described previously in example 1, and expression of the viral antigens is analyzed by radioimmunoprecipitation using an anti-West Nile mouse immune serum, according to conventional protocols as described in Duarte Dos Santos et al. (Virology, 2000, 274: 292-308).

The results show that 80% of the neurons in culture produce the viral antigens:
their SDS-polyacrylamide gel profile is given in FIG. 4A;
the viral production is $[3.0±1.5]×10^6$ FFU/ml after 20 h of infection and $[7.0±0.5]×10^7$ FFU/ml at 40 h;
the cytopathic effects (CPEs) of the necrotic type are observed after 48 h of viral infection.

On the other hand, astrocytes of the murine CNS are not permissive to replication of the WN virus strain IS-98-ST1.

$b_2$) Cell Lines

Neuro 2a murine neuroblastoma cells and HepG2 human hepatoma cells, cultured under conventional conditions as described in Marianneau et al. (J. Virol., 1996, 77: 2547-2554), are infected at various multiplicities of infection with the WN virus strain IS-98-ST1, prepared as described in example 1. The cytopathic effect is observed by light microscopy, viral production is analyzed by titering on AP61 cells as previously described in example 1, and expression of the viral antigens is analyzed by radioimmunoprecipitation using an anti-West Nile mouse immune serum, according to conventional protocols as described in Duarte Dos Santos et al., Virol., 2000, 274, 292-308.

The results show that Neuro 2a murine neuroblastoma cells are permissive to replication of the strain IS-98-ST1 of the WN virus. An m.i. of 4 is necessary to infect 80% of the Neuro 2a cells in monolayer. The viral production is $10^7$ FFU/ml (m.i. of 4) after 40 h of infection, and there is massive cell death by necrosis (FIG. 5). The kinetics of production of the major antigens prM, E and NS1 from the viral polyprotein, given in FIG. 4B, shows that the half-time of formation of the envelope glycoprotein E is approximately 30 min. The E protein of the strain IS-98-ST1 appears to have only one N-glycan residue (FIG. 4C).

The results also show that HepG2 human hepatoma cells are permissive to replication of the strain IS-98-ST1 of the WN virus. At an m.i. of 10, the viral production is $[2±1]×10^6$ FFU/ml after 48 h of infection and the CPEs are observed from 72 h.

2—Resistant Mice

The resistant ($Flv^r$) mouse lines which derive from wild mice of the species Mus spretus (SEG/Pas and STF/Pas), Mus musculus musculus (MBT/Pas, MAI/pas) and Mus musculus domesticus (WMP/Pas) are inoculated intraperitoneally with 1 000 FFU (100 LD50) of the strain IS-98-ST1 prepared according to the protocol described in example 1.

Unlike the laboratory mice which are sensitive to infection with the strain IS-98-ST1 and die in about ten days, these mice derived from wild mice are resistant to inoculation with the strain IS-98-ST1 and, nevertheless, permissive to replication of the strain IS-98-ST1. In fact, viral infection of the mice derived from wild mice is asymptomatic, although the virus multiplies, in toto, as demonstrated by the production of anti-WN serum antibodies at high titers; by ELISA, the titers of the sera at a dilution of 1:100, for $10^6$ FFU of purified IS-98-ST1 virion, are greater than 1 O.D. unit at 450 nm.

The mice resistant to viral infection are used to produce immune sera specifically directed against the proteins of the strain IS-98-ST1 of the WN virus. Three weeks after inoculation with the WN virus, the sera taken from resistant mice (0.045 ml per mouse) are mixed, decomplemented for 30 min at 56° C. and then diluted to 1:10 in DPBS* (v/v) supplemented with 0.2% (v/v) of bovine serum albumin (Life Technologies) and 0.05% (w/v) of sodium azide. The diluted sera are divided up into 0.2 ml aliquots and stored at −20° C. The immune sera directed against the strain IS-98-ST1 are used at the final dilutions of 1:500 for indirect immunofluorescence and at 1:1 000 for immunoprecipitation of radiolabeled viral proteins.

EXAMPLE 5

Use of the Strain IS-98-ST1 of the West Nile Virus to Identify the Cellular Genes Involved in Host Sensitivity to Infection with Viruses of the Family Flaviviridae 1) Methods a) Model for Analyzing Resistance to Infection with Flaviviridae (FIG. 6)

Male mice of the resistant lines MAI/Pas and MBT/Pas are crossed with female mice of the sensitive lines C57BL/6 and BALB/c. The male mice of the F1 generation are backcrossed with female mice of the sensitive lines C57BL/6 and BALB/c, to give a generation of first backcross (BC1) mice.

Five-week-old BC1 mice are inoculated intraperitoneally with the strain IS-98-ST1, prepared according to the protocol described in example 1, under the conditions described in example 2.

The animals are observed every day and the mortality and survival rates are determined 14 days after infection.

b) Genotyping of Flv Alleles

The Flv alleles of the BC1 individuals were mapped by genomic PCR using primers specific for 16 microsatellites of chromosome 5 (Catalogue Research Genetics) surrounding the Flv locus (FIGS. 7-9), according to common techniques of molecular biology using standard protocols such as those described in *Current Protocols in Molecular Biology* (Frederick M. AUSUBEL, 2000, Wiley and Son Inc. Library of Congress, USA).

2) Results

Analysis of Flv allele distribution in the BC1 mice sensitive and resistant to infection with the strain IS-98ST1 shows that one Flv$^r$ allele is sufficient to confer resistance to infection (FIG. 10). The results also show that, in this model, a perfect correlation exists between the resistant phenotype and the presence of the Flv$^r$ allele and an almost perfect correlation exists between the sensitive phenotype and the absence of the Flv$^r$ allele (FIG. 10).

The genotyping of the Flv alleles shows that the Flv locus is located in a 0.2 cM region containing the OAS1 gene (FIGS. 7-9).

---

The invention claimed is:

1. An isolated strain of the West Nile virus, wherein its genome consists of the sequence SEQ ID No. 1.

2. A nucleic acid molecule, selected from the group consisting of the sequence SEQ ID No. 1 and the antisense sequence complementary to SEQ ID No. 1.

3. An isolated eukaryotic cell, transformed with a nucleic acid molecule consisting of SEQ. ID NO. 1, the antisense sequence complementary to SEQ ID NO: 1, a vector comprising SEQ ID NO: 1, a vector comprising the antisense sequence complementary to SEQ ID NO: 1, or a neurovirulent strain of the West Nile virus comprising SEQ ID NO:1.

4. A model for studying sensitivity/resistance to infection with a virus of the family Flaviviridae, comprising at least the West Nile virus as claimed in claim 1.

5. The study model as claimed in claim 4, further comprising a mouse homozygous for the $FIV^r$ or $Flv^s$ allele.

6. A variant of an isolated strain of the West Nile virus, wherein its genome consists of the sequence SEQ ID NO: 1 with only the nucleotide sequence corresponding to the NS5 protein containing at least one mutation.

* * * * *

SEQUENCE LISTING

<160> NUMBER OF SEQ ID NOS: 12

<210> SEQ ID NO 1
<211> LENGTH: 11029
<212> TYPE: DNA
<213> ORGANISM: Flavivirus sp.
<220> FEATURE:
<221> NAME/KEY: CDS
<222> LOCATION: (97)..(10395)

<400> SEQUENCE: 1

```
agtagttcgc ctgtgtgagc tgacaaactt agtagtgttt gtgaggatta acaacaatta      60
acacagtgcg agctgtttct tagcacgaag atctcg atg tct aag aaa cca gga        114
                                        Met Ser Lys Lys Pro Gly
                                         1               5 ggg ccc ggc aag agc cgg gct gtc aat atg cta aaa cgc gga atg ccc        162
Gly Pro Gly Lys Ser Arg Ala Val Asn Met Leu Lys Arg Gly Met Pro
             10                  15                  20 cgc gtg ttg tcc ttg att gga ctg aag agg gct atg ttg agc ctg atc        210
Arg Val Leu Ser Leu Ile Gly Leu Lys Arg Ala Met Leu Ser Leu Ile
         25                  30                  35 gac ggc aag ggg cca ata cga ttt gtg ttg gct ctc ttg gcg ttc ttc        258
Asp Gly Lys Gly Pro Ile Arg Phe Val Leu Ala Leu Leu Ala Phe Phe
     40                  45                  50 agg ttc aca gca att gct ccg acc cga gca gtg ctg gat cga tgg aga        306
Arg Phe Thr Ala Ile Ala Pro Thr Arg Ala Val Leu Asp Arg Trp Arg
 55                  60                  65                  70 ggt gtg aat aaa caa aca gcg atg aaa cac ctt ctg agt ttt aag aag        354
Gly Val Asn Lys Gln Thr Ala Met Lys His Leu Leu Ser Phe Lys Lys
                 75                  80                  85 gaa cta ggg acc ttg acc agt gct atc aat cgg cgg agc tca aaa caa        402
Glu Leu Gly Thr Leu Thr Ser Ala Ile Asn Arg Arg Ser Ser Lys Gln
             90                  95                 100
```

| | | | | | | | | | | | | | | | |
|---|---|---|---|---|---|---|---|---|---|---|---|---|---|---|---|
| aag | aaa | aga | gga | gga | aag | acc | gga | att | gca | gtc | atg | att | ggc | ctg | atc | 450
| Lys | Lys | Arg | Gly | Gly | Lys | Thr | Gly | Ile | Ala | Val | Met | Ile | Gly | Leu | Ile |
| | | 105 | | | | 110 | | | | 115 | | | | | |

```
aag aaa aga gga gga aag acc gga att gca gtc atg att ggc ctg atc      450
Lys Lys Arg Gly Gly Lys Thr Gly Ile Ala Val Met Ile Gly Leu Ile
        105                 110                 115 gcc agc gta gga gca gtt acc ctc tct aac ttc caa ggg aag gtg atg      498
Ala Ser Val Gly Ala Val Thr Leu Ser Asn Phe Gln Gly Lys Val Met
120                 125                 130 atg acg gta aat gct act gac gtc aca gat gtc atc acg att cca aca      546
Met Thr Val Asn Ala Thr Asp Val Thr Asp Val Ile Thr Ile Pro Thr
135                 140                 145                 150 gct gct gga aag aac cta tgc att gtc aga gca atg gat gtg gga tac      594
Ala Ala Gly Lys Asn Leu Cys Ile Val Arg Ala Met Asp Val Gly Tyr
                155                 160                 165 atg tgc gat gat act atc act tat gaa tgc cca gtg ctg tcg gct ggt      642
Met Cys Asp Asp Thr Ile Thr Tyr Glu Cys Pro Val Leu Ser Ala Gly
            170                 175                 180 aat gat cca gaa gac atc gac tgt tgg tgc aca aag tca gca gtc tac      690
Asn Asp Pro Glu Asp Ile Asp Cys Trp Cys Thr Lys Ser Ala Val Tyr
        185                 190                 195 gtc agg tat gga aga tgc acc aag aca cgc cac tca aga cgc agt cgg      738
Val Arg Tyr Gly Arg Cys Thr Lys Thr Arg His Ser Arg Arg Ser Arg
    200                 205                 210 agg tca ctg aca gtg cag aca cac gga gaa agc act cta gcg aac aag      786
Arg Ser Leu Thr Val Gln Thr His Gly Glu Ser Thr Leu Ala Asn Lys
215                 220                 225                 230 aag ggg gct tgg atg gac agc acc aag gcc aca agg tat ttg gta aaa      834
Lys Gly Ala Trp Met Asp Ser Thr Lys Ala Thr Arg Tyr Leu Val Lys
                235                 240                 245 aca gaa tca tgg atc ttg agg aac cct gga tat gcc ctg gtg gca gcc      882
Thr Glu Ser Trp Ile Leu Arg Asn Pro Gly Tyr Ala Leu Val Ala Ala
            250                 255                 260 gtc att ggt tgg atg ctt ggg agc aac acc atg cag aga gtt gtg ttt      930
Val Ile Gly Trp Met Leu Gly Ser Asn Thr Met Gln Arg Val Val Phe
        265                 270                 275 gtc gtg cta ttg ctt ttg gtg gcc cca gct tac agc ttt aac tgc ctt      978
Val Val Leu Leu Leu Leu Val Ala Pro Ala Tyr Ser Phe Asn Cys Leu
    280                 285                 290 gga atg agc aac aga gac ttc ttg gaa gga gtg tct gga gca aca tgg      1026
Gly Met Ser Asn Arg Asp Phe Leu Glu Gly Val Ser Gly Ala Thr Trp
295                 300                 305                 310 gtg gat ttg gtt ctc gaa ggc gac agc tgc gtg act atc atg tct aag      1074
Val Asp Leu Val Leu Glu Gly Asp Ser Cys Val Thr Ile Met Ser Lys
                315                 320                 325 gac aag cct acc atc gat gtg aag atg atg aat atg gag gcg gcc aac      1122
Asp Lys Pro Thr Ile Asp Val Lys Met Met Asn Met Glu Ala Ala Asn
            330                 335                 340 ctg gca gag gtc cgc agt tat tgc tat ttg gct acc gtc agc gat ctc      1170
Leu Ala Glu Val Arg Ser Tyr Cys Tyr Leu Ala Thr Val Ser Asp Leu
        345                 350                 355 tcc acc aaa gct gcg tgc ccg acc atg gga gaa gct cac aat gac aaa      1218
Ser Thr Lys Ala Ala Cys Pro Thr Met Gly Glu Ala His Asn Asp Lys
    360                 365                 370 cgt gct gac cca gct ttt gtg tgc aga caa gga gtg gtg gac agg ggc      1266
Arg Ala Asp Pro Ala Phe Val Cys Arg Gln Gly Val Val Asp Arg Gly
375                 380                 385                 390 tgg ggc aac ggc tgc gga cta ttt ggc aaa gga agc att gac aca tgc      1314
Trp Gly Asn Gly Cys Gly Leu Phe Gly Lys Gly Ser Ile Asp Thr Cys
                395                 400                 405 gcc aaa ttt gcc tgc tct acc aag gca ata gga aga acc atc ttg aaa      1362
Ala Lys Phe Ala Cys Ser Thr Lys Ala Ile Gly Arg Thr Ile Leu Lys
```

```
                     410                 415                 420
gag aat atc aag tac gaa gtg gcc att ttt gtc cat gga cca act act      1410
Glu Asn Ile Lys Tyr Glu Val Ala Ile Phe Val His Gly Pro Thr Thr
            425                 430                 435 gtg gag tcg cac gga aac tac tcc aca cag gtt gga gcc act cag gca      1458
Val Glu Ser His Gly Asn Tyr Ser Thr Gln Val Gly Ala Thr Gln Ala
    440                 445                 450 ggg aga ttc agc atc act cct gcg gcg cct tca tac aca cta aag ctt      1506
Gly Arg Phe Ser Ile Thr Pro Ala Ala Pro Ser Tyr Thr Leu Lys Leu
455                 460                 465                 470 gga gaa tat gga gag gtg aca gtg gac tgt gaa cca cgg tca ggg att      1554
Gly Glu Tyr Gly Glu Val Thr Val Asp Cys Glu Pro Arg Ser Gly Ile
                475                 480                 485 gac acc aat gca tac tac gtg atg act gtt gga aca aag acg ttc ttg      1602
Asp Thr Asn Ala Tyr Tyr Val Met Thr Val Gly Thr Lys Thr Phe Leu
            490                 495                 500 gtc cat cgt gag tgg ttc atg gac ctc aac ctc cct tgg agc agt gct      1650
Val His Arg Glu Trp Phe Met Asp Leu Asn Leu Pro Trp Ser Ser Ala
    505                 510                 515 gga agt act gtg tgg agg aac aga gag acg tta atg gag ttt gag gaa      1698
Gly Ser Thr Val Trp Arg Asn Arg Glu Thr Leu Met Glu Phe Glu Glu
520                 525                 530 cca cac gcc acg aag cag tct gtg ata gca ttg ggc tca caa gag gga      1746
Pro His Ala Thr Lys Gln Ser Val Ile Ala Leu Gly Ser Gln Glu Gly
535                 540                 545                 550 gct ctg cat caa gct ttg gct gga gcc att cct gtg gaa ttt tca agc      1794
Ala Leu His Gln Ala Leu Ala Gly Ala Ile Pro Val Glu Phe Ser Ser
                555                 560                 565 aac act gtc aag ttg acg tcg ggt cat ttg aag tgt aga gtg aag atg      1842
Asn Thr Val Lys Leu Thr Ser Gly His Leu Lys Cys Arg Val Lys Met
            570                 575                 580 gaa aaa ttg cag ttg aag gga aca acc tat ggc gtc tgt tca aag gct      1890
Glu Lys Leu Gln Leu Lys Gly Thr Thr Tyr Gly Val Cys Ser Lys Ala
    585                 590                 595 ttc aag ttt ctt ggg act ccc gca gac aca ggt cac ggc act gtg gtg      1938
Phe Lys Phe Leu Gly Thr Pro Ala Asp Thr Gly His Gly Thr Val Val
600                 605                 610 ttg gaa ttg cag tac act ggc acg gat gga cct tgc aaa gtt cct atc      1986
Leu Glu Leu Gln Tyr Thr Gly Thr Asp Gly Pro Cys Lys Val Pro Ile
615                 620                 625                 630 tcg tca gtg gct tca ttg aac gac cta acg cca gtg ggc aga ttg gtc      2034
Ser Ser Val Ala Ser Leu Asn Asp Leu Thr Pro Val Gly Arg Leu Val
                635                 640                 645 act gtc aac cct ttt gtt tca gtg gcc acg gcc aac gct aag gtc ctg      2082
Thr Val Asn Pro Phe Val Ser Val Ala Thr Ala Asn Ala Lys Val Leu
            650                 655                 660 att gaa ttg gaa cca ccc ttt gga gac tca tac ata gtg gtg ggc aga      2130
Ile Glu Leu Glu Pro Pro Phe Gly Asp Ser Tyr Ile Val Val Gly Arg
    665                 670                 675 gga gaa caa cag att aat cac cat tgg cac aag tct gga agc agc att      2178
Gly Glu Gln Gln Ile Asn His His Trp His Lys Ser Gly Ser Ser Ile
680                 685                 690 ggc aaa gcc ttt aca acc acc ctc aaa gga gcg cag aga cta gcc gct      2226
Gly Lys Ala Phe Thr Thr Thr Leu Lys Gly Ala Gln Arg Leu Ala Ala
695                 700                 705                 710 cta gga gac aca gct tgg gac ttt gga tca gtt gga ggg gtg ttc acc      2274
Leu Gly Asp Thr Ala Trp Asp Phe Gly Ser Val Gly Gly Val Phe Thr
                715                 720                 725 tca gtt ggg aag gct gtc cat caa gtg ttc gga gga gca ttc cgc tca      2322
```

```
            Ser Val Gly Lys Ala Val His Gln Val Phe Gly Gly Ala Phe Arg Ser
                        730                 735                 740 ctg ttc gga ggc atg tcc tgg ata acg caa gga ttg ctg ggg gct ctc          2370
Leu Phe Gly Gly Met Ser Trp Ile Thr Gln Gly Leu Leu Gly Ala Leu
            745                 750                 755 ctg ttg tgg atg ggc atc aat gct cgt gat agg tcc ata gct ctc acg          2418
Leu Leu Trp Met Gly Ile Asn Ala Arg Asp Arg Ser Ile Ala Leu Thr
        760                 765                 770 ttt ctc gca gtt gga gga gtt ctg ctc ttc ctc tcc gtg aac gtg cac          2466
Phe Leu Ala Val Gly Gly Val Leu Leu Phe Leu Ser Val Asn Val His
775                 780                 785                 790 gct gac act ggg tgt gcc ata gac atc agc cgg caa gag ctg aga tgt          2514
Ala Asp Thr Gly Cys Ala Ile Asp Ile Ser Arg Gln Glu Leu Arg Cys
                795                 800                 805 gga aat gga gtg ttc ata cac aat gat gtg gag gct tgg atg gac cgg          2562
Gly Asn Gly Val Phe Ile His Asn Asp Val Glu Ala Trp Met Asp Arg
            810                 815                 820 tac aag tat tac cct gaa acg cca caa ggc cta gcc aag atc att cag          2610
Tyr Lys Tyr Tyr Pro Glu Thr Pro Gln Gly Leu Ala Lys Ile Ile Gln
        825                 830                 835 aaa gct cat aag gaa gga gtg tgc ggt cta cga tca gtt tcc aga ctg          2658
Lys Ala His Lys Glu Gly Val Cys Gly Leu Arg Ser Val Ser Arg Leu
    840                 845                 850 gag cat caa atg tgg gaa gca gtg aag gac gag ctg aac act ctt ttg          2706
Glu His Gln Met Trp Glu Ala Val Lys Asp Glu Leu Asn Thr Leu Leu
855                 860                 865                 870 aag gag aat ggt gtg gac ctt agt gtc gtg gtt gag aaa cag gag gga          2754
Lys Glu Asn Gly Val Asp Leu Ser Val Val Glu Lys Gln Glu Gly
                875                 880                 885 atg tac aag tca gca cct aaa cgc ctc acc gcc acc acg gaa aaa ttg          2802
Met Tyr Lys Ser Ala Pro Lys Arg Leu Thr Ala Thr Thr Glu Lys Leu
            890                 895                 900 gaa att ggc tgg aag gcc tgg gga aag agt att tta ttt gca cca gaa          2850
Glu Ile Gly Trp Lys Ala Trp Gly Lys Ser Ile Leu Phe Ala Pro Glu
        905                 910                 915 ctc gcc aac aac acc ttt gtg gtt gat ggt ccg gag acc aag gaa tgt          2898
Leu Ala Asn Asn Thr Phe Val Val Asp Gly Pro Glu Thr Lys Glu Cys
    920                 925                 930 ccg act cag aat cgc gct tgg aat agc tta gaa gtg gag gat ttt gga          2946
Pro Thr Gln Asn Arg Ala Trp Asn Ser Leu Glu Val Glu Asp Phe Gly
935                 940                 945                 950 ttt ggt ctc acc agc act cgg atg ttc ctg aag gtc aga gag agc aac          2994
Phe Gly Leu Thr Ser Thr Arg Met Phe Leu Lys Val Arg Glu Ser Asn
                955                 960                 965 aca act gaa tgt gac tcg aag atc att gga acg gct gtc aag aac aac          3042
Thr Thr Glu Cys Asp Ser Lys Ile Ile Gly Thr Ala Val Lys Asn Asn
            970                 975                 980 ttg gcg atc cac agt gac ctg tcc tat tgg att gaa agc agg ctc aat          3090
Leu Ala Ile His Ser Asp Leu Ser Tyr Trp Ile Glu Ser Arg Leu Asn
        985                 990                 995 gat acg tgg aag ctt gaa agg  gca gtt ctg ggt gaa  gtc aaa tca            3135
Asp Thr Trp Lys Leu Glu Arg  Ala Val Leu Gly Glu  Val Lys Ser
    1000                1005                     1010 tgt acg tgg cct gag acg cat  acc ttg tgg ggc gat  gga atc ctt            3180
Cys Thr Trp Pro Glu Thr His  Thr Leu Trp Gly Asp  Gly Ile Leu
    1015                1020                     1025 gag agt gac ttg ata ata cca  gtc aca ctg gcg gga  cca cga agc            3225
Glu Ser Asp Leu Ile Ile Pro  Val Thr Leu Ala Gly  Pro Arg Ser
    1030                1035                     1040
```

```
aat cac aat cgg aga cct ggg tac aag aca caa aac cag ggc cca      3270
Asn His Asn Arg Arg Pro Gly Tyr Lys Thr Gln Asn Gln Gly Pro
    1045            1050                1055 tgg gac gaa ggc cgg gta gag att gac ttc gat tac tgc cca gga      3315
Trp Asp Glu Gly Arg Val Glu Ile Asp Phe Asp Tyr Cys Pro Gly
    1060            1065                1070 act acg gtc acc ctg agt gag agc tgc gga cac cgt gga cct gcc      3360
Thr Thr Val Thr Leu Ser Glu Ser Cys Gly His Arg Gly Pro Ala
    1075            1080                1085 act cgc acc acc aca gag agc gga aag ttg ata aca gat tgg tgc      3405
Thr Arg Thr Thr Thr Glu Ser Gly Lys Leu Ile Thr Asp Trp Cys
    1090            1095                1100 tgc agg agc tgc acc tta cca cca ctg cgc tac caa act gac agc      3450
Cys Arg Ser Cys Thr Leu Pro Pro Leu Arg Tyr Gln Thr Asp Ser
    1105            1110                1115 ggc tgt tgg tat ggt atg gag atc aga cca cag aga cat gat gaa      3495
Gly Cys Trp Tyr Gly Met Glu Ile Arg Pro Gln Arg His Asp Glu
    1120            1125                1130 aag acc ctc gtg cag tca caa gtg aat gct tat aat gct gat atg      3540
Lys Thr Leu Val Gln Ser Gln Val Asn Ala Tyr Asn Ala Asp Met
    1135            1140                1145 att gac cct ttt cag ttg ggc ctt ctg gtc gtg ttc ttg gcc acc      3585
Ile Asp Pro Phe Gln Leu Gly Leu Leu Val Val Phe Leu Ala Thr
    1150            1155                1160 cag gag gtc ctt cgc aag agg tgg aca gcc aag atc agc atg cca      3630
Gln Glu Val Leu Arg Lys Arg Trp Thr Ala Lys Ile Ser Met Pro
    1165            1170                1175 gct ata ctg att gct ctg cta gtc ctg gtg ttt ggg ggc att act      3675
Ala Ile Leu Ile Ala Leu Leu Val Leu Val Phe Gly Gly Ile Thr
    1180            1185                1190 tac act gat gtg tta cgc tat gtc atc ttg gtg ggg gca gct ttc      3720
Tyr Thr Asp Val Leu Arg Tyr Val Ile Leu Val Gly Ala Ala Phe
    1195            1200                1205 gca gaa tct aat tcg gga gga gac gtg gta cac ttg gcg ctc atg      3765
Ala Glu Ser Asn Ser Gly Gly Asp Val Val His Leu Ala Leu Met
    1210            1215                1220 gcg acc ttc aag ata caa cca gtg ttt atg gtg gca tcg ttt ctc      3810
Ala Thr Phe Lys Ile Gln Pro Val Phe Met Val Ala Ser Phe Leu
    1225            1230                1235 aaa gcg aga tgg acc aac cag gag aac att ttg ttg atg ttg gcg      3855
Lys Ala Arg Trp Thr Asn Gln Glu Asn Ile Leu Leu Met Leu Ala
    1240            1245                1250 gct gtt ttc ttt caa atg gct tat cac gat gcc cgc caa att ctg      3900
Ala Val Phe Phe Gln Met Ala Tyr His Asp Ala Arg Gln Ile Leu
    1255            1260                1265 ctc tgg gag atc cct gat gtg ttg aat tca ctg gcg gta gct tgg      3945
Leu Trp Glu Ile Pro Asp Val Leu Asn Ser Leu Ala Val Ala Trp
    1270            1275                1280 atg ata ctg aga gcc ata aca ttc aca acg aca tca aat gtg gtc      3990
Met Ile Leu Arg Ala Ile Thr Phe Thr Thr Thr Ser Asn Val Val
    1285            1290                1295 gtc ccg ctg cta gcc ctg cta aca ccc cgg ctg aga tgc ttg aat      4035
Val Pro Leu Leu Ala Leu Leu Thr Pro Arg Leu Arg Cys Leu Asn
    1300            1305                1310 ctg gat gtg tac agg ata ctg ctg ttg atg gtc gga ata ggc agc      4080
Leu Asp Val Tyr Arg Ile Leu Leu Met Val Gly Ile Gly Ser
    1315            1320                1325 ttg atc agg gag aag agg agt gca gct gca aaa aag aaa gga gca      4125
Leu Ile Arg Glu Lys Arg Ser Ala Ala Ala Lys Lys Lys Gly Ala
    1330            1335                1340
```

| | | | | | | | | | | | | |
|---|---|---|---|---|---|---|---|---|---|---|---|---|
| agt | ctg | cta | tgc | ttg | gct | cta | gcc | tca | aca | gga | ctt | ttc aac ccc | 4170 |
| Ser | Leu | Leu | Cys | Leu | Ala | Leu | Ala | Ser | Thr | Gly | Leu | Phe Asn Pro |
| | 1345 | | | | 1350 | | | | | 1355 | | |

| atg | atc | ctt | gct | gct | gga | ctg | att | gca | tgt | gat | ccc | aac cgt aaa | 4215 |
| Met | Ile | Leu | Ala | Ala | Gly | Leu | Ile | Ala | Cys | Asp | Pro | Asn Arg Lys |
| 1360 | | | | | 1365 | | | | | 1370 | | |

| cgc | gga | tgg | ccc | gca | act | gaa | gtg | atg | aca | gct | gtc | ggc cta atg | 4260 |
| Arg | Gly | Trp | Pro | Ala | Thr | Glu | Val | Met | Thr | Ala | Val | Gly Leu Met |
| 1375 | | | | | 1380 | | | | | 1385 | | |

| ttt | gcc | atc | gtc | gga | ggg | ctg | gca | gag | ctt | gac | att | gac tcc atg | 4305 |
| Phe | Ala | Ile | Val | Gly | Gly | Leu | Ala | Glu | Leu | Asp | Ile | Asp Ser Met |
| 1390 | | | | | 1395 | | | | | 1400 | | |

| gcc | att | cca | atg | act | atc | gcg | ggg | ctc | atg | ttt | gct | gct ttc gtg | 4350 |
| Ala | Ile | Pro | Met | Thr | Ile | Ala | Gly | Leu | Met | Phe | Ala | Ala Phe Val |
| 1405 | | | | | 1410 | | | | | 1415 | | |

| att | tct | ggg | aaa | tca | aca | gat | atg | tgg | att | gag | aga | acg gcg gac | 4395 |
| Ile | Ser | Gly | Lys | Ser | Thr | Asp | Met | Trp | Ile | Glu | Arg | Thr Ala Asp |
| 1420 | | | | | 1425 | | | | | 1430 | | |

| att | tcc | tgg | gaa | agt | gat | gca | gaa | att | aca | ggc | tcg | agc gaa aga | 4440 |
| Ile | Ser | Trp | Glu | Ser | Asp | Ala | Glu | Ile | Thr | Gly | Ser | Ser Glu Arg |
| 1435 | | | | | 1440 | | | | | 1445 | | |

| gtt | gat | gtt | cgg | ctt | gat | gat | ggt | gaa | aac | ttc | cag | ctc atg aat | 4485 |
| Val | Asp | Val | Arg | Leu | Asp | Asp | Gly | Glu | Asn | Phe | Gln | Leu Met Asn |
| 1450 | | | | | 1455 | | | | | 1460 | | |

| gat | cca | gga | gca | cct | tgg | aag | ata | tgg | atg | ctc | aga | atg gtc tgt | 4530 |
| Asp | Pro | Gly | Ala | Pro | Trp | Lys | Ile | Trp | Met | Leu | Arg | Met Val Cys |
| 1465 | | | | | 1470 | | | | | 1475 | | |

| ctc | gcg | att | agt | gcg | tac | acc | ccc | tgg | gca | atc | ttg | ccc tca gta | 4575 |
| Leu | Ala | Ile | Ser | Ala | Tyr | Thr | Pro | Trp | Ala | Ile | Leu | Pro Ser Val |
| 1480 | | | | | 1485 | | | | | 1490 | | |

| gtt | gga | ttt | tgg | ata | act | ctc | caa | tac | aca | aag | aga | gga ggt gtg | 4620 |
| Val | Gly | Phe | Trp | Ile | Thr | Leu | Gln | Tyr | Thr | Lys | Arg | Gly Gly Val |
| 1495 | | | | | 1500 | | | | | 1505 | | |

| ttg | tgg | gac | act | ccc | tca | cca | aag | gag | tac | aaa | aag | ggg gac acg | 4665 |
| Leu | Trp | Asp | Thr | Pro | Ser | Pro | Lys | Glu | Tyr | Lys | Lys | Gly Asp Thr |
| 1510 | | | | | 1515 | | | | | 1520 | | |

| acc | acc | ggc | gtc | tac | agg | atc | atg | act | cgt | ggg | ctg | ctc ggc agt | 4710 |
| Thr | Thr | Gly | Val | Tyr | Arg | Ile | Met | Thr | Arg | Gly | Leu | Leu Gly Ser |
| 1525 | | | | | 1530 | | | | | 1535 | | |

| tat | caa | gca | gga | gcg | ggc | gtg | atg | gtt | gaa | ggt | gtt | ttc cac acc | 4755 |
| Tyr | Gln | Ala | Gly | Ala | Gly | Val | Met | Val | Glu | Gly | Val | Phe His Thr |
| 1540 | | | | | 1545 | | | | | 1550 | | |

| ctt | tgg | cat | aca | aca | aaa | gga | gcc | gct | ttg | atg | agc | gga gag ggc | 4800 |
| Leu | Trp | His | Thr | Thr | Lys | Gly | Ala | Ala | Leu | Met | Ser | Gly Glu Gly |
| 1555 | | | | | 1560 | | | | | 1565 | | |

| cgc | ctg | gac | cca | tac | tgg | ggc | agt | gtc | aag | gag | gat | cga ctt tgt | 4845 |
| Arg | Leu | Asp | Pro | Tyr | Trp | Gly | Ser | Val | Lys | Glu | Asp | Arg Leu Cys |
| 1570 | | | | | 1575 | | | | | 1580 | | |

| tac | gga | gga | ccc | tgg | aaa | ttg | cag | cac | aag | tgg | aac | ggg cag gat | 4890 |
| Tyr | Gly | Gly | Pro | Trp | Lys | Leu | Gln | His | Lys | Trp | Asn | Gly Gln Asp |
| 1585 | | | | | 1590 | | | | | 1595 | | |

| gag | gtg | cag | atg | att | gtg | gtg | gaa | cct | ggc | aag | aac | gtt aag aac | 4935 |
| Glu | Val | Gln | Met | Ile | Val | Val | Glu | Pro | Gly | Lys | Asn | Val Lys Asn |
| 1600 | | | | | 1605 | | | | | 1610 | | |

| gtc | cag | acg | aaa | cca | ggg | gtg | ttc | aaa | aca | cct | gaa | gga gaa atc | 4980 |
| Val | Gln | Thr | Lys | Pro | Gly | Val | Phe | Lys | Thr | Pro | Glu | Gly Glu Ile |
| 1615 | | | | | 1620 | | | | | 1625 | | |

| ggg | gcc | gtg | act | ttg | gac | ttc | ccc | act | gga | aca | tca | ggc tca cca | 5025 |
| Gly | Ala | Val | Thr | Leu | Asp | Phe | Pro | Thr | Gly | Thr | Ser | Gly Ser Pro |

-continued

```
         1630                1635                1640
ata gtg gac aaa aac ggt gat gtg att ggg ctt tat ggc aat gga      5070
Ile Val Asp Lys Asn Gly Asp Val Ile Gly Leu Tyr Gly Asn Gly
    1645                1650                1655 gtc ata atg ccc aac ggc tca tac ata agc gcg ata gtg cag ggt      5115
Val Ile Met Pro Asn Gly Ser Tyr Ile Ser Ala Ile Val Gln Gly
    1660                1665                1670 gaa agg atg gat gag cca atc cca gcc gga ttc gaa cct gag atg      5160
Glu Arg Met Asp Glu Pro Ile Pro Ala Gly Phe Glu Pro Glu Met
    1675                1680                1685 ctg agg aaa aaa cag atc act gta ctg gat ctc cat ccc ggc gcc      5205
Leu Arg Lys Lys Gln Ile Thr Val Leu Asp Leu His Pro Gly Ala
    1690                1695                1700 ggt aaa aca agg agg att ctg cca cag atc atc aaa gag gcc ata      5250
Gly Lys Thr Arg Arg Ile Leu Pro Gln Ile Ile Lys Glu Ala Ile
    1705                1710                1715 aac aga aga ctg aga aca gcc gtg cta gca cca acc agg gtt gtg      5295
Asn Arg Arg Leu Arg Thr Ala Val Leu Ala Pro Thr Arg Val Val
    1720                1725                1730 gct gct gag atg gct gaa gca ctg aga gga ctg ccc atc cgg tac      5340
Ala Ala Glu Met Ala Glu Ala Leu Arg Gly Leu Pro Ile Arg Tyr
    1735                1740                1745 cag aca tcc gca gtg ccc aga gaa cat aat gga aat gag att gtt      5385
Gln Thr Ser Ala Val Pro Arg Glu His Asn Gly Asn Glu Ile Val
    1750                1755                1760 gat gtc atg tgt cat gct acc ctc acc cac agg ctg atg tct cct      5430
Asp Val Met Cys His Ala Thr Leu Thr His Arg Leu Met Ser Pro
    1765                1770                1775 cac agg gtg ccg aac tac aac ctg ttc gtg atg gat gag gct cat      5475
His Arg Val Pro Asn Tyr Asn Leu Phe Val Met Asp Glu Ala His
    1780                1785                1790 ttc acc gac cca gct agt atc gca gca aga ggt tac att tcc aca      5520
Phe Thr Asp Pro Ala Ser Ile Ala Ala Arg Gly Tyr Ile Ser Thr
    1795                1800                1805 aag gtc gag cta ggg gag gcg gcg gca ata ttc atg aca gcc acc      5565
Lys Val Glu Leu Gly Glu Ala Ala Ala Ile Phe Met Thr Ala Thr
    1810                1815                1820 cca cca ggc act tca gat cca ttc cca gag tcc aat tca cca att      5610
Pro Pro Gly Thr Ser Asp Pro Phe Pro Glu Ser Asn Ser Pro Ile
    1825                1830                1835 tcc gac tta cag act gag atc ccg gat cga gct tgg aac tct gga      5655
Ser Asp Leu Gln Thr Glu Ile Pro Asp Arg Ala Trp Asn Ser Gly
    1840                1845                1850 tac gaa tgg atc aca gaa tac acc ggg aag acg gtt tgg ttt gtg      5700
Tyr Glu Trp Ile Thr Glu Tyr Thr Gly Lys Thr Val Trp Phe Val
    1855                1860                1865 cct agt gtc aag atg ggg aat gag att gcc ctt tgc cta caa cgt      5745
Pro Ser Val Lys Met Gly Asn Glu Ile Ala Leu Cys Leu Gln Arg
    1870                1875                1880 gct gga aag aaa gta gtc caa ttg aac aga aag tcg tac gag acg      5790
Ala Gly Lys Lys Val Val Gln Leu Asn Arg Lys Ser Tyr Glu Thr
    1885                1890                1895 gag tac cca aaa tgt aag aac gat gat tgg gac ttt gtt atc aca      5835
Glu Tyr Pro Lys Cys Lys Asn Asp Asp Trp Asp Phe Val Ile Thr
    1900                1905                1910 aca gac ata tct gaa atg ggg gct aac ttc aag gcg agc agg gtg      5880
Thr Asp Ile Ser Glu Met Gly Ala Asn Phe Lys Ala Ser Arg Val
    1915                1920                1925 att gac agc cgg aag agt gtg aaa cca acc atc ata aca gaa gga      5925
```

```
Ile Asp Ser Arg Lys Ser Val Lys Pro Thr Ile Ile Thr Glu Gly
    1930            1935            1940 gaa ggg aga gtg atc ctg gga gaa cca tct gca gtg aca gca gct    5970
Glu Gly Arg Val Ile Leu Gly Glu Pro Ser Ala Val Thr Ala Ala
    1945            1950            1955 agt gcc gcc cag aga cgt gga cgt atc ggt aga aat ccg tcg caa    6015
Ser Ala Ala Gln Arg Arg Gly Arg Ile Gly Arg Asn Pro Ser Gln
    1960            1965            1970 gtt ggt gat gag tac tgt tat ggg ggg cac acg aat gaa gac gac    6060
Val Gly Asp Glu Tyr Cys Tyr Gly Gly His Thr Asn Glu Asp Asp
    1975            1980            1985 tcg aac ttc gcc cat tgg act gag gca cga atc atg ccg gac aac    6105
Ser Asn Phe Ala His Trp Thr Glu Ala Arg Ile Met Pro Asp Asn
    1990            1995            2000 atc aac atg cca aac gga ctg atc gct caa ttc tac caa cca gag    6150
Ile Asn Met Pro Asn Gly Leu Ile Ala Gln Phe Tyr Gln Pro Glu
    2005            2010            2015 cgt gag aag gta tat acc atg gag ggg gaa tac cgg ctc aga gga    6195
Arg Glu Lys Val Tyr Thr Met Glu Gly Glu Tyr Arg Leu Arg Gly
    2020            2025            2030 gaa gag agg aaa aac ttt ctg gaa ctg ttg agg act gca gat ctg    6240
Glu Glu Arg Lys Asn Phe Leu Glu Leu Leu Arg Thr Ala Asp Leu
    2035            2040            2045 cca gtt tgg ctg gct tac aag gtt gca gcg gct gga gtg tca tac    6285
Pro Val Trp Leu Ala Tyr Lys Val Ala Ala Ala Gly Val Ser Tyr
    2050            2055            2060 cac gac cgg agg tgg tgc ttt gat ggt cct agg aca aac aca att    6330
His Asp Arg Arg Trp Cys Phe Asp Gly Pro Arg Thr Asn Thr Ile
    2065            2070            2075 tta gaa gac aac aac gaa gtg gaa gtc atc acg aag ctt ggt gaa    6375
Leu Glu Asp Asn Asn Glu Val Glu Val Ile Thr Lys Leu Gly Glu
    2080            2085            2090 agg aag att ctg agg ccg cgc tgg att gac gcc agg gtg tac tcg    6420
Arg Lys Ile Leu Arg Pro Arg Trp Ile Asp Ala Arg Val Tyr Ser
    2095            2100            2105 gat cac cag gca cta aag gcg ttc aag gac ttc gcc tcg gga aaa    6465
Asp His Gln Ala Leu Lys Ala Phe Lys Asp Phe Ala Ser Gly Lys
    2110            2115            2120 cgt tct cag ata ggg ctc att gag gtt ctg gga aag atg cct gag    6510
Arg Ser Gln Ile Gly Leu Ile Glu Val Leu Gly Lys Met Pro Glu
    2125            2130            2135 cac ttc atg ggg aag aca tgg gaa gca ctt gac acc atg tac gtt    6555
His Phe Met Gly Lys Thr Trp Glu Ala Leu Asp Thr Met Tyr Val
    2140            2145            2150 gtg gcc act gca gag aaa gga gga aga gct cac aga atg gcc ctg    6600
Val Ala Thr Ala Glu Lys Gly Gly Arg Ala His Arg Met Ala Leu
    2155            2160            2165 gag gaa ctg cca gat gct ctt cag aca att gcc ttg att gcc tta    6645
Glu Glu Leu Pro Asp Ala Leu Gln Thr Ile Ala Leu Ile Ala Leu
    2170            2175            2180 ttg agt gtg atg acc atg gga gta ttc ttc ctc ctc atg cag cgg    6690
Leu Ser Val Met Thr Met Gly Val Phe Phe Leu Leu Met Gln Arg
    2185            2190            2195 aag ggc att gga aag ata ggt ttg gga ggc gct gtc ttg gga gtc    6735
Lys Gly Ile Gly Lys Ile Gly Leu Gly Gly Ala Val Leu Gly Val
    2200            2205            2210 gcg acc ttt ttc tgt tgg atg gct gaa gtt cca gga acg aag atc    6780
Ala Thr Phe Phe Cys Trp Met Ala Glu Val Pro Gly Thr Lys Ile
    2215            2220            2225
```

```
gcc gga atg ttg ctg ctc tcc ctt ctc ttg atg att gtg cta att      6825
Ala Gly Met Leu Leu Leu Ser Leu Leu Leu Met Ile Val Leu Ile
    2230                2235                2240 cct gag cca gag aag caa cgt tcg cag aca gac aac cag cta gcc      6870
Pro Glu Pro Glu Lys Gln Arg Ser Gln Thr Asp Asn Gln Leu Ala
2245                2250                2255 gtg ttc ctg att tgt gtc atg acc ctt gtg agc gca gtg gca gcc      6915
Val Phe Leu Ile Cys Val Met Thr Leu Val Ser Ala Val Ala Ala
    2260                2265                2270 aac gag atg ggt tgg cta gac aag acc aag agt gac ata agc agt      6960
Asn Glu Met Gly Trp Leu Asp Lys Thr Lys Ser Asp Ile Ser Ser
2275                2280                2285 ttg ttt ggg caa aga att gag gtc aag gag aat ttc agc atg gga      7005
Leu Phe Gly Gln Arg Ile Glu Val Lys Glu Asn Phe Ser Met Gly
    2290                2295                2300 gag ttt ctt ctg gac ttg agg ccg gca aca gcc tgg tca ctg tac      7050
Glu Phe Leu Leu Asp Leu Arg Pro Ala Thr Ala Trp Ser Leu Tyr
2305                2310                2315 gct gtg aca aca gcg gtc ctc act cca ctg cta aag cat ttg atc      7095
Ala Val Thr Thr Ala Val Leu Thr Pro Leu Leu Lys His Leu Ile
    2320                2325                2330 acg tca gat tac atc aac acc tca ttg acc tca ata aac gtt cag      7140
Thr Ser Asp Tyr Ile Asn Thr Ser Leu Thr Ser Ile Asn Val Gln
2335                2340                2345 gca agt gca cta ttc aca ctc gcg cga ggc ttc ccc ttc gtc gat      7185
Ala Ser Ala Leu Phe Thr Leu Ala Arg Gly Phe Pro Phe Val Asp
    2350                2355                2360 gtt gga gtg tcg gct ctc ctg cta gca gcc gga tgc tgg gga caa      7230
Val Gly Val Ser Ala Leu Leu Leu Ala Ala Gly Cys Trp Gly Gln
2365                2370                2375 gtc acc ctc acc gtt acg gta aca gcg gca aca ctc ctt ttt tgc      7275
Val Thr Leu Thr Val Thr Val Thr Ala Ala Thr Leu Leu Phe Cys
    2380                2385                2390 cac tat gcc tac atg gtt ccc ggt tgg caa gct gag gca atg cgc      7320
His Tyr Ala Tyr Met Val Pro Gly Trp Gln Ala Glu Ala Met Arg
2395                2400                2405 tca gcc cag cgg cgg aca gcg gcc gga atc atg aaa aac gct gta      7365
Ser Ala Gln Arg Arg Thr Ala Ala Gly Ile Met Lys Asn Ala Val
    2410                2415                2420 gtg gat ggc atc gtg gcc acg gac gtc cca gaa tta gag cgc acc      7410
Val Asp Gly Ile Val Ala Thr Asp Val Pro Glu Leu Glu Arg Thr
2425                2430                2435 aca ccc atc atg cag aag aaa gtt gga cag atc atg ctg atc ttg      7455
Thr Pro Ile Met Gln Lys Lys Val Gly Gln Ile Met Leu Ile Leu
    2440                2445                2450 gtg tct cta gct gca gta gta gtg aac ccg tct gtg aag aca gta      7500
Val Ser Leu Ala Ala Val Val Val Asn Pro Ser Val Lys Thr Val
2455                2460                2465 cga gaa gcc gga att ttg atc acg gcc gca gcg gtg acg ctt tgg      7545
Arg Glu Ala Gly Ile Leu Ile Thr Ala Ala Ala Val Thr Leu Trp
    2470                2475                2480 gag aat gga gca agc tct gtt tgg aac gca aca act gcc atc gga      7590
Glu Asn Gly Ala Ser Ser Val Trp Asn Ala Thr Thr Ala Ile Gly
2485                2490                2495 ctc tgc cac atc atg cgt ggg ggt tgg ttg tca tgt cta tcc ata      7635
Leu Cys His Ile Met Arg Gly Gly Trp Leu Ser Cys Leu Ser Ile
    2500                2505                2510 aca tgg aca ctc ata aag aac atg gaa aaa cca gga cta aaa aga      7680
Thr Trp Thr Leu Ile Lys Asn Met Glu Lys Pro Gly Leu Lys Arg
2515                2520                2525
```

```
ggt ggg gca aaa gga cgc acc ttg gga gag gtt tgg aaa gaa aga      7725
Gly Gly Ala Lys Gly Arg Thr Leu Gly Glu Val Trp Lys Glu Arg
        2530                2535                2540 ctc aac cag atg aca aaa gaa gag ttc act agg tac cgc aaa gag      7770
Leu Asn Gln Met Thr Lys Glu Glu Phe Thr Arg Tyr Arg Lys Glu
    2545                2550                2555 gcc atc atc gaa gtc gat cgc tca gcg gca aaa cac gcc agg aaa      7815
Ala Ile Ile Glu Val Asp Arg Ser Ala Ala Lys His Ala Arg Lys
2560                2565                2570 gaa ggc aat gtc act gga ggg cat tca gtc tct agg ggc aca gca      7860
Glu Gly Asn Val Thr Gly Gly His Ser Val Ser Arg Gly Thr Ala
        2575                2580                2585 aaa ctg aga tgg ctg gtc gaa cgg agg ttt ctc gaa ccg gtc gga      7905
Lys Leu Arg Trp Leu Val Glu Arg Arg Phe Leu Glu Pro Val Gly
    2590                2595                2600 aaa gtg att gac ctt gga tgt gga aga ggc ggt tgg tgt tac tat      7950
Lys Val Ile Asp Leu Gly Cys Gly Arg Gly Gly Trp Cys Tyr Tyr
2605                2610                2615 atg gca acc caa aaa aga gtc caa gaa gtc aga ggg tac aca aag      7995
Met Ala Thr Gln Lys Arg Val Gln Glu Val Arg Gly Tyr Thr Lys
        2620                2625                2630 ggc ggt ccc gga cat gaa gag ccc caa cta gtc caa agt tat gga      8040
Gly Gly Pro Gly His Glu Glu Pro Gln Leu Val Gln Ser Tyr Gly
    2635                2640                2645 tgg aac att gtc acc atg aag agt gga gtg gat gtg ttc tac aga      8085
Trp Asn Ile Val Thr Met Lys Ser Gly Val Asp Val Phe Tyr Arg
2650                2655                2660 cct tct gag tgt tgt gac acc ctc ctt tgt gac atc gga gag tcc      8130
Pro Ser Glu Cys Cys Asp Thr Leu Leu Cys Asp Ile Gly Glu Ser
        2665                2670                2675 tcg tca agt gct gag gtt gaa gag cat agg acg att cgt gtc ctt      8175
Ser Ser Ser Ala Glu Val Glu Glu His Arg Thr Ile Arg Val Leu
    2680                2685                2690 gaa atg gtt gag gac tgg ctg cac cga ggg cca agg gaa ttt tgc      8220
Glu Met Val Glu Asp Trp Leu His Arg Gly Pro Arg Glu Phe Cys
2695                2700                2705 gtg aag gtg ctc tgc ccc tac atg ccg aaa gtc ata gag aag atg      8265
Val Lys Val Leu Cys Pro Tyr Met Pro Lys Val Ile Glu Lys Met
        2710                2715                2720 gag ctg ctc caa cgc cgg tat ggg ggg gga ctg gtc aga aac cca      8310
Glu Leu Leu Gln Arg Arg Tyr Gly Gly Gly Leu Val Arg Asn Pro
    2725                2730                2735 ctc tca cgg aat tcc acg cac gag atg tat tgg gtg agt cga gct      8355
Leu Ser Arg Asn Ser Thr His Glu Met Tyr Trp Val Ser Arg Ala
2740                2745                2750 tca ggc aat gtg gta cat tca gtg aat atg acc agc cag gtg ctc      8400
Ser Gly Asn Val Val His Ser Val Asn Met Thr Ser Gln Val Leu
        2755                2760                2765 cta gga aga atg gaa aaa agg acc tgg aag gga ccc caa tac gag      8445
Leu Gly Arg Met Glu Lys Arg Thr Trp Lys Gly Pro Gln Tyr Glu
    2770                2775                2780 gaa gat gta aac ttg gga agc gga acc agg gcg gtg gga aaa ccc      8490
Glu Asp Val Asn Leu Gly Ser Gly Thr Arg Ala Val Gly Lys Pro
2785                2790                2795 ctg ctc aac tca gac acc agt aaa atc aac aac agg att gaa cga      8535
Leu Leu Asn Ser Asp Thr Ser Lys Ile Asn Asn Arg Ile Glu Arg
        2800                2805                2810 ctc agg cgt gag tac agt tcg acg tgg cac cac gat gag aac cac      8580
Leu Arg Arg Glu Tyr Ser Ser Thr Trp His His Asp Glu Asn His
```

-continued

| | | | | | | | | | | | |
|---|---|---|---|---|---|---|---|---|---|---|---|
| | 2815 | | | 2820 | | | | 2825 | | | |
| cca<br>Pro<br>2830 | tat<br>Tyr | aga<br>Arg | acc<br>Thr | tgg<br>Trp | aac<br>Asn<br>2835 | tat<br>Tyr | cac<br>His | ggc<br>Gly | agt<br>Ser | tat<br>Tyr | gat<br>Asp<br>2840 | gtg<br>Val | aag<br>Lys | ccc<br>Pro | 8625 |
| aca<br>Thr<br>2845 | ggc<br>Gly | tcc<br>Ser | gcc<br>Ala | agt<br>Ser | tcg<br>Ser<br>2850 | ctg<br>Leu | gtc<br>Val | aat<br>Asn | gga<br>Gly | gtg<br>Val | gtc<br>Val<br>2855 | agg<br>Arg | ctc<br>Leu | ctc<br>Leu | 8670 |
| tca<br>Ser<br>2860 | aaa<br>Lys | cca<br>Pro | tgg<br>Trp | gac<br>Asp | acc<br>Thr<br>2865 | atc<br>Ile | acg<br>Thr | aat<br>Asn | gtt<br>Val | acc<br>Thr | acc<br>Thr<br>2870 | atg<br>Met | gcc<br>Ala | atg<br>Met | 8715 |
| act<br>Thr<br>2875 | gac<br>Asp | act<br>Thr | act<br>Thr | ccc<br>Pro | ttc<br>Phe<br>2880 | ggg<br>Gly | cag<br>Gln | cag<br>Gln | cga<br>Arg | gtg<br>Val | ttc<br>Phe<br>2885 | aaa<br>Lys | gag<br>Glu | aag<br>Lys | 8760 |
| gtg<br>Val<br>2890 | gac<br>Asp | acg<br>Thr | aaa<br>Lys | gct<br>Ala | cct<br>Pro<br>2895 | gaa<br>Glu | ccg<br>Pro | cca<br>Pro | gaa<br>Glu | gga<br>Gly | gcg<br>Ala<br>2900 | aag<br>Lys | tac<br>Tyr | gtg<br>Val | 8805 |
| ctc<br>Leu<br>2905 | aac<br>Asn | gag<br>Glu | acc<br>Thr | acc<br>Thr | aac<br>Asn<br>2910 | tgg<br>Trp | ttg<br>Leu | tgg<br>Trp | gcg<br>Ala | ttt<br>Phe | ttg<br>Leu<br>2915 | gcc<br>Ala | aga<br>Arg | gaa<br>Glu | 8850 |
| aaa<br>Lys<br>2920 | cgt<br>Arg | ccc<br>Pro | aga<br>Arg | atg<br>Met | tgc<br>Cys<br>2925 | tct<br>Ser | cga<br>Arg | gag<br>Glu | gaa<br>Glu | ttc<br>Phe | ata<br>Ile<br>2930 | aga<br>Arg | aag<br>Lys | gtc<br>Val | 8895 |
| aac<br>Asn<br>2935 | agc<br>Ser | aat<br>Asn | gca<br>Ala | gct<br>Ala | ttg<br>Leu<br>2940 | ggt<br>Gly | gcc<br>Ala | atg<br>Met | ttt<br>Phe | gaa<br>Glu | gag<br>Glu<br>2945 | cag<br>Gln | aat<br>Asn | caa<br>Gln | 8940 |
| tgg<br>Trp<br>2950 | agg<br>Arg | agc<br>Ser | gcc<br>Ala | aga<br>Arg | gaa<br>Glu<br>2955 | gca<br>Ala | gtt<br>Val | gaa<br>Glu | gat<br>Asp | cca<br>Pro | aaa<br>Lys<br>2960 | ttt<br>Phe | tgg<br>Trp | gag<br>Glu | 8985 |
| atg<br>Met<br>2965 | gtg<br>Val | gat<br>Asp | gag<br>Glu | gag<br>Glu | cgc<br>Arg<br>2970 | gag<br>Glu | gca<br>Ala | cat<br>His | ctg<br>Leu | cgg<br>Arg | ggg<br>Gly<br>2975 | gaa<br>Glu | tgt<br>Cys | cac<br>His | 9030 |
| act<br>Thr<br>2980 | tgc<br>Cys | att<br>Ile | tac<br>Tyr | aac<br>Asn | atg<br>Met<br>2985 | atg<br>Met | gga<br>Gly | aag<br>Lys | aga<br>Arg | gag<br>Glu | aaa<br>Lys<br>2990 | aaa<br>Lys | ccc<br>Pro | gga<br>Gly | 9075 |
| gag<br>Glu<br>2995 | ttc<br>Phe | gga<br>Gly | aag<br>Lys | gcc<br>Ala | aag<br>Lys<br>3000 | gga<br>Gly | agc<br>Ser | aga<br>Arg | gcc<br>Ala | att<br>Ile | tgg<br>Trp<br>3005 | ttc<br>Phe | atg<br>Met | tgg<br>Trp | 9120 |
| ctc<br>Leu<br>3010 | gga<br>Gly | gct<br>Ala | cgc<br>Arg | ttt<br>Phe | ctg<br>Leu<br>3015 | gag<br>Glu | ttc<br>Phe | gag<br>Glu | gct<br>Ala | ctg<br>Leu | ggt<br>Gly<br>3020 | ttt<br>Phe | ctc<br>Leu | aat<br>Asn | 9165 |
| gaa<br>Glu<br>3025 | gac<br>Asp | cac<br>His | tgg<br>Trp | ctt<br>Leu | gga<br>Gly<br>3030 | aga<br>Arg | aag<br>Lys | aac<br>Asn | tca<br>Ser | gga<br>Gly | gga<br>Gly<br>3035 | ggt<br>Gly | gtc<br>Val | gag<br>Glu | 9210 |
| ggc<br>Gly<br>3040 | ttg<br>Leu | ggc<br>Gly | ctc<br>Leu | caa<br>Gln | aaa<br>Lys<br>3045 | ctg<br>Leu | ggt<br>Gly | tac<br>Tyr | atc<br>Ile | ctg<br>Leu | cgt<br>Arg<br>3050 | gaa<br>Glu | gtt<br>Val | ggc<br>Gly | 9255 |
| acc<br>Thr<br>3055 | cgg<br>Arg | cct<br>Pro | ggg<br>Gly | ggc<br>Gly | aag<br>Lys<br>3060 | atc<br>Ile | tat<br>Tyr | gct<br>Ala | gat<br>Asp | gac<br>Asp | aca<br>Thr<br>3065 | gct<br>Ala | ggc<br>Gly | tgg<br>Trp | 9300 |
| gac<br>Asp<br>3070 | acc<br>Thr | cgc<br>Arg | atc<br>Ile | acg<br>Thr | aga<br>Arg<br>3075 | gct<br>Ala | gac<br>Asp | ttg<br>Leu | gaa<br>Glu | aat<br>Asn | gaa<br>Glu<br>3080 | gct<br>Ala | aag<br>Lys | gtg<br>Val | 9345 |
| ctt<br>Leu<br>3085 | gag<br>Glu | ctg<br>Leu | ctt<br>Leu | gat<br>Asp | ggg<br>Gly<br>3090 | gaa<br>Glu | cat<br>His | cgg<br>Arg | cgt<br>Arg | ctt<br>Leu | gcc<br>Ala<br>3095 | agg<br>Arg | gcc<br>Ala | atc<br>Ile | 9390 |
| att<br>Ile<br>3100 | gag<br>Glu | ctc<br>Leu | acc<br>Thr | tat<br>Tyr | cgt<br>Arg<br>3105 | cac<br>His | aaa<br>Lys | gtt<br>Val | gtg<br>Val | aaa<br>Lys | gtg<br>Val<br>3110 | atg<br>Met | cgc<br>Arg | ccg<br>Pro | 9435 |
| gct<br>Ala | gct<br>Ala | gat<br>Asp | gga<br>Gly | aga<br>Arg | acc<br>Thr | gtc<br>Val | atg<br>Met | gat<br>Asp | gtt<br>Val | atc<br>Ile | tcc<br>Ser | aga<br>Arg | gaa<br>Glu | gat<br>Asp | 9480 |

```
         Ala Ala Asp Gly Arg Thr Val Met Asp Val Ile Ser Arg Glu Asp
             3115                3120                3125 cag agg ggg agt gga caa gtt gtc acc tac gcc cta aac act ttc          9525
Gln Arg Gly Ser Gly Gln Val Val Thr Tyr Ala Leu Asn Thr Phe
    3130                3135                3140 acc aac ctg gcc gtc cag ctg gtg agg atg atg gaa ggg gaa gga          9570
Thr Asn Leu Ala Val Gln Leu Val Arg Met Met Glu Gly Glu Gly
    3145                3150                3155 gtg att ggc cca gat gat gtg gag aaa ctc aca aaa ggg aaa gga          9615
Val Ile Gly Pro Asp Asp Val Glu Lys Leu Thr Lys Gly Lys Gly
    3160                3165                3170 ccc aaa gtc agg acc tgg ctg ttt gag aat ggg gaa gaa aga ctc          9660
Pro Lys Val Arg Thr Trp Leu Phe Glu Asn Gly Glu Glu Arg Leu
    3175                3180                3185 agc cgc atg gct gtc agt gga gat gac tgt gtg gta aag ccc ctg          9705
Ser Arg Met Ala Val Ser Gly Asp Asp Cys Val Val Lys Pro Leu
    3190                3195                3200 gac gat cgc ttt gcc acc tcg ctc cac ttc ctc aat gct atg tca          9750
Asp Asp Arg Phe Ala Thr Ser Leu His Phe Leu Asn Ala Met Ser
    3205                3210                3215 aag gtt cgc aaa gac atc caa gag tgg aaa ccg tca act gga tgg          9795
Lys Val Arg Lys Asp Ile Gln Glu Trp Lys Pro Ser Thr Gly Trp
    3220                3225                3230 tat gat tgg cag cag gtt cca ttt tgc tca aac cat ttc act gaa          9840
Tyr Asp Trp Gln Gln Val Pro Phe Cys Ser Asn His Phe Thr Glu
    3235                3240                3245 ttg atc atg aaa gat gga aga aca ctg gtg gtt cca tgc cga gga          9885
Leu Ile Met Lys Asp Gly Arg Thr Leu Val Val Pro Cys Arg Gly
    3250                3255                3260 cag gat gaa ttg gta ggc aga gct cgc ata tct cca ggg gcc gga          9930
Gln Asp Glu Leu Val Gly Arg Ala Arg Ile Ser Pro Gly Ala Gly
    3265                3270                3275 tgg aac gtc cgc gac act gct tgt ctg gct aag tct tat gcc cag          9975
Trp Asn Val Arg Asp Thr Ala Cys Leu Ala Lys Ser Tyr Ala Gln
    3280                3285                3290 atg tgg ctg ctt ctg tac ttc cac aga aga gac ctg cgg ctc atg         10020
Met Trp Leu Leu Leu Tyr Phe His Arg Arg Asp Leu Arg Leu Met
    3295                3300                3305 gcc aac gcc att tgc tcc gct gtc cct gtg aat tgg gtc cct acc         10065
Ala Asn Ala Ile Cys Ser Ala Val Pro Val Asn Trp Val Pro Thr
    3310                3315                3320 gga aga acc acg tgg tcc atc cat gca gga gga gag tgg atg aca         10110
Gly Arg Thr Thr Trp Ser Ile His Ala Gly Gly Glu Trp Met Thr
    3325                3330                3335 aca gag gac atg ttg gag gtc tgg aac cgt gtt tgg ata gag gag         10155
Thr Glu Asp Met Leu Glu Val Trp Asn Arg Val Trp Ile Glu Glu
    3340                3345                3350 aat gaa tgg atg gaa gac aaa acc cca gtg gag aaa tgg agt gac         10200
Asn Glu Trp Met Glu Asp Lys Thr Pro Val Glu Lys Trp Ser Asp
    3355                3360                3365 gtc cca tat tca gga aaa cga gag gac atc tgg tgt ggc agc ctg         10245
Val Pro Tyr Ser Gly Lys Arg Glu Asp Ile Trp Cys Gly Ser Leu
    3370                3375                3380 att ggc aca aga gcc cga gcc acg tgg gca gaa aac atc cag gtg         10290
Ile Gly Thr Arg Ala Arg Ala Thr Trp Ala Glu Asn Ile Gln Val
    3385                3390                3395 gct atc aac caa gtc aga gca atc atc gga gat gag aag tat gtg         10335
Ala Ile Asn Gln Val Arg Ala Ile Ile Gly Asp Glu Lys Tyr Val
    3400                3405                3410
```

-continued

```
gat tac  atg agt tca cta aag  aga tat gaa gac aca  act ttg gtt     10380
Asp Tyr  Met Ser Ser Leu Lys  Arg Tyr Glu Asp Thr  Thr Leu Val
    3415                3420                3425 gag gac  aca gta ctg tagatattta atcaattgta aatagacaat ataagtatgc   10435
Glu Asp  Thr Val Leu
    3430 ataaaagtgt agttttatag tagtatttag tggtgttagt gtaaatagtt aagaaaattt  10495 tgaggagaaa gtcaggccgg gaagttcccg ccaccggaag ttgagtagac ggtgctgcct  10555 gcgactcaac cccaggagga ctgggtgaac aaagccgcga agtgatccat gtaagccctc  10615 agaaccgtct cggaaggagg accccacatg ttgtaacttc aaagcccaat gtcagaccac  10675 gctacggcgt gctactctgc ggagagtgca gtctgcgata gtgccccagg aggactgggt  10735 taacaaaggc aaaccaacgc cccacgcggc cctagccccg gtaatggtgt taaccagggc  10795 gaaaggacta gaggttagag gagaccccgc ggtttaaagt gcacggccca gcctgactga  10855 agctgtaggt caggggaagg actagaggtt agtggagacc ccgtgccaca aaacaccaca  10915 acaaaaacagc atattgacac ctgggataga ctaggagatc ttctgctctg cacaaccagc 10975 cacacggcac agtgcgccga caatggtggc tggtggtgcg agaacacagg atct        11029

<210> SEQ ID NO 2
<211> LENGTH: 3433
<212> TYPE: PRT
<213> ORGANISM: Flavivirus sp.

<400> SEQUENCE: 2

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
    130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
        195                 200                 205

His Ser Arg Arg Ser Arg Arg Ser Leu Thr Val Gln Thr His Gly Glu
    210                 215                 220

Ser Thr Leu Ala Asn Lys Lys Gly Ala Trp Met Asp Ser Thr Lys Ala
```

-continued

```
            225                 230                 235                 240
Thr Arg Tyr Leu Val Lys Thr Glu Ser Trp Ile Leu Arg Asn Pro Gly
                245                 250                 255
Tyr Ala Leu Val Ala Ala Val Ile Gly Trp Met Leu Gly Ser Asn Thr
                260                 265                 270
Met Gln Arg Val Val Phe Val Leu Leu Leu Val Ala Pro Ala
            275                 280                 285
Tyr Ser Phe Asn Cys Leu Gly Met Ser Asn Arg Asp Phe Leu Glu Gly
            290                 295                 300
Val Ser Gly Ala Thr Trp Val Asp Leu Val Leu Glu Gly Asp Ser Cys
305                 310                 315                 320
Val Thr Ile Met Ser Lys Asp Lys Pro Thr Ile Asp Val Lys Met Met
                325                 330                 335
Asn Met Glu Ala Ala Asn Leu Ala Glu Val Arg Ser Tyr Cys Tyr Leu
                340                 345                 350
Ala Thr Val Ser Asp Leu Ser Thr Lys Ala Ala Cys Pro Thr Met Gly
                355                 360                 365
Glu Ala His Asn Asp Lys Arg Ala Asp Pro Ala Phe Val Cys Arg Gln
                370                 375                 380
Gly Val Val Asp Arg Gly Trp Gly Asn Gly Cys Gly Leu Phe Gly Lys
385                 390                 395                 400
Gly Ser Ile Asp Thr Cys Ala Lys Phe Ala Cys Ser Thr Lys Ala Ile
                405                 410                 415
Gly Arg Thr Ile Leu Lys Glu Asn Ile Lys Tyr Glu Val Ala Ile Phe
                420                 425                 430
Val His Gly Pro Thr Thr Val Glu Ser His Gly Asn Tyr Ser Thr Gln
                435                 440                 445
Val Gly Ala Thr Gln Ala Gly Arg Phe Ser Ile Thr Pro Ala Ala Pro
                450                 455                 460
Ser Tyr Thr Leu Lys Leu Gly Glu Tyr Gly Glu Val Thr Val Asp Cys
465                 470                 475                 480
Glu Pro Arg Ser Gly Ile Asp Thr Asn Ala Tyr Tyr Val Met Thr Val
                485                 490                 495
Gly Thr Lys Thr Phe Leu Val His Arg Glu Trp Phe Met Asp Leu Asn
                500                 505                 510
Leu Pro Trp Ser Ser Ala Gly Ser Thr Val Trp Arg Asn Arg Glu Thr
                515                 520                 525
Leu Met Glu Phe Glu Glu Pro His Ala Thr Lys Gln Ser Val Ile Ala
                530                 535                 540
Leu Gly Ser Gln Glu Gly Ala Leu His Gln Ala Leu Ala Gly Ala Ile
545                 550                 555                 560
Pro Val Glu Phe Ser Ser Asn Thr Val Lys Leu Thr Ser Gly His Leu
                565                 570                 575
Lys Cys Arg Val Lys Met Glu Lys Leu Gln Leu Lys Gly Thr Thr Tyr
                580                 585                 590
Gly Val Cys Ser Lys Ala Phe Lys Phe Leu Gly Thr Pro Ala Asp Thr
                595                 600                 605
Gly His Gly Thr Val Val Leu Glu Leu Gln Tyr Thr Gly Thr Asp Gly
                610                 615                 620
Pro Cys Lys Val Pro Ile Ser Ser Val Ala Ser Leu Asn Asp Leu Thr
625                 630                 635                 640
Pro Val Gly Arg Leu Val Thr Val Asn Pro Phe Val Ser Val Ala Thr
                645                 650                 655
```

-continued

```
Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
        675                 680                 685

Lys Ser Gly Ser Ser Ile Gly Lys Ala Phe Thr Thr Thr Leu Lys Gly
        690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
                740                 745                 750

Gly Leu Leu Gly Ala Leu Leu Leu Trp Met Gly Ile Asn Ala Arg Asp
            755                 760                 765

Arg Ser Ile Ala Leu Thr Phe Leu Ala Val Gly Gly Val Leu Leu Phe
    770                 775                 780

Leu Ser Val Asn Val His Ala Asp Thr Gly Cys Ala Ile Asp Ile Ser
785                 790                 795                 800

Arg Gln Glu Leu Arg Cys Gly Asn Gly Val Phe Ile His Asn Asp Val
                805                 810                 815

Glu Ala Trp Met Asp Arg Tyr Lys Tyr Tyr Pro Glu Thr Pro Gln Gly
                820                 825                 830

Leu Ala Lys Ile Ile Gln Lys Ala His Lys Glu Gly Val Cys Gly Leu
            835                 840                 845

Arg Ser Val Ser Arg Leu Glu His Gln Met Trp Glu Ala Val Lys Asp
850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
                885                 890                 895

Ala Thr Thr Glu Lys Leu Glu Ile Gly Trp Lys Ala Trp Gly Lys Ser
            900                 905                 910

Ile Leu Phe Ala Pro Glu Leu Ala Asn Asn Thr Phe Val Val Asp Gly
        915                 920                 925

Pro Glu Thr Lys Glu Cys Pro Thr Gln Asn Arg Ala Trp Asn Ser Leu
        930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
                965                 970                 975

Thr Ala Val Lys Asn Asn Leu Ala Ile His Ser Asp Leu Ser Tyr Trp
            980                 985                 990

Ile Glu Ser Arg Leu Asn Asp Thr  Trp Lys Leu Glu Arg  Ala Val Leu
        995                 1000                1005

Gly Glu  Val Lys Ser Cys Thr  Trp Pro Glu Thr His  Thr Leu Trp
    1010                1015                1020

Gly Asp  Gly Ile Leu Glu Ser  Asp Leu Ile Ile Pro  Val Thr Leu
    1025                1030                1035

Ala Gly  Pro Arg Ser Asn His  Asn Arg Arg Pro Gly  Tyr Lys Thr
    1040                1045                1050

Gln Asn  Gln Gly Pro Trp Asp  Glu Gly Arg Val Glu  Ile Asp Phe
    1055                1060                1065
```

-continued

```
Asp Tyr Cys Pro Gly Thr Val Thr Leu Ser Glu Ser Cys Gly
1070                1075                1080

His Arg Gly Pro Ala Thr Arg Thr Thr Thr Glu Ser Gly Lys Leu
1085                1090                1095

Ile Thr Asp Trp Cys Cys Arg Ser Cys Thr Leu Pro Pro Leu Arg
1100                1105                1110

Tyr Gln Thr Asp Ser Gly Cys Trp Tyr Gly Met Glu Ile Arg Pro
1115                1120                1125

Gln Arg His Asp Glu Lys Thr Leu Val Gln Ser Gln Val Asn Ala
1130                1135                1140

Tyr Asn Ala Asp Met Ile Asp Pro Phe Gln Leu Gly Leu Leu Val
1145                1150                1155

Val Phe Leu Ala Thr Gln Glu Val Leu Arg Lys Arg Trp Thr Ala
1160                1165                1170

Lys Ile Ser Met Pro Ala Ile Leu Ile Ala Leu Leu Val Leu Val
1175                1180                1185

Phe Gly Gly Ile Thr Tyr Thr Asp Val Leu Arg Tyr Val Ile Leu
1190                1195                1200

Val Gly Ala Ala Phe Ala Glu Ser Asn Ser Gly Gly Asp Val Val
1205                1210                1215

His Leu Ala Leu Met Ala Thr Phe Lys Ile Gln Pro Val Phe Met
1220                1225                1230

Val Ala Ser Phe Leu Lys Ala Arg Trp Thr Asn Gln Glu Asn Ile
1235                1240                1245

Leu Leu Met Leu Ala Ala Val Phe Phe Gln Met Ala Tyr His Asp
1250                1255                1260

Ala Arg Gln Ile Leu Leu Trp Glu Ile Pro Asp Val Leu Asn Ser
1265                1270                1275

Leu Ala Val Ala Trp Met Ile Leu Arg Ala Ile Thr Phe Thr Thr
1280                1285                1290

Thr Ser Asn Val Val Pro Leu Leu Ala Leu Leu Thr Pro Arg
1295                1300                1305

Leu Arg Cys Leu Asn Leu Asp Val Tyr Arg Ile Leu Leu Leu Met
1310                1315                1320

Val Gly Ile Gly Ser Leu Ile Arg Glu Lys Arg Ser Ala Ala Ala
1325                1330                1335

Lys Lys Lys Gly Ala Ser Leu Leu Cys Leu Ala Leu Ala Ser Thr
1340                1345                1350

Gly Leu Phe Asn Pro Met Ile Leu Ala Ala Gly Leu Ile Ala Cys
1355                1360                1365

Asp Pro Asn Arg Lys Arg Gly Trp Pro Ala Thr Glu Val Met Thr
1370                1375                1380

Ala Val Gly Leu Met Phe Ala Ile Val Gly Gly Leu Ala Glu Leu
1385                1390                1395

Asp Ile Asp Ser Met Ala Ile Pro Met Thr Ile Ala Gly Leu Met
1400                1405                1410

Phe Ala Ala Phe Val Ile Ser Gly Lys Ser Thr Asp Met Trp Ile
1415                1420                1425

Glu Arg Thr Ala Asp Ile Ser Trp Glu Ser Asp Ala Glu Ile Thr
1430                1435                1440

Gly Ser Ser Glu Arg Val Asp Val Arg Leu Asp Asp Gly Glu Asn
1445                1450                1455

Phe Gln Leu Met Asn Asp Pro Gly Ala Pro Trp Lys Ile Trp Met
```

-continued

```
            1460                1465                1470

Leu Arg Met Val Cys Leu Ala Ile Ser Ala Tyr Thr Pro Trp Ala
    1475                1480                1485

Ile Leu Pro Ser Val Val Gly Phe Trp Ile Thr Leu Gln Tyr Thr
    1490                1495                1500

Lys Arg Gly Gly Val Leu Trp Asp Thr Pro Ser Pro Lys Glu Tyr
    1505                1510                1515

Lys Lys Gly Asp Thr Thr Thr Gly Val Tyr Arg Ile Met Thr Arg
    1520                1525                1530

Gly Leu Leu Gly Ser Tyr Gln Ala Gly Ala Gly Val Met Val Glu
    1535                1540                1545

Gly Val Phe His Thr Leu Trp His Thr Thr Lys Gly Ala Ala Leu
    1550                1555                1560

Met Ser Gly Glu Gly Arg Leu Asp Pro Tyr Trp Gly Ser Val Lys
    1565                1570                1575

Glu Asp Arg Leu Cys Tyr Gly Gly Pro Trp Lys Leu Gln His Lys
    1580                1585                1590

Trp Asn Gly Gln Asp Glu Val Gln Met Ile Val Val Glu Pro Gly
    1595                1600                1605

Lys Asn Val Lys Asn Val Gln Thr Lys Pro Gly Val Phe Lys Thr
    1610                1615                1620

Pro Glu Gly Glu Ile Gly Ala Val Thr Leu Asp Phe Pro Thr Gly
    1625                1630                1635

Thr Ser Gly Ser Pro Ile Val Asp Lys Asn Gly Asp Val Ile Gly
    1640                1645                1650

Leu Tyr Gly Asn Gly Val Ile Met Pro Asn Gly Ser Tyr Ile Ser
    1655                1660                1665

Ala Ile Val Gln Gly Glu Arg Met Asp Glu Pro Ile Pro Ala Gly
    1670                1675                1680

Phe Glu Pro Glu Met Leu Arg Lys Lys Gln Ile Thr Val Leu Asp
    1685                1690                1695

Leu His Pro Gly Ala Gly Lys Thr Arg Arg Ile Leu Pro Gln Ile
    1700                1705                1710

Ile Lys Glu Ala Ile Asn Arg Arg Leu Arg Thr Ala Val Leu Ala
    1715                1720                1725

Pro Thr Arg Val Val Ala Ala Glu Met Ala Glu Ala Leu Arg Gly
    1730                1735                1740

Leu Pro Ile Arg Tyr Gln Thr Ser Ala Val Pro Arg Glu His Asn
    1745                1750                1755

Gly Asn Glu Ile Val Asp Val Met Cys His Ala Thr Leu Thr His
    1760                1765                1770

Arg Leu Met Ser Pro His Arg Val Pro Asn Tyr Asn Leu Phe Val
    1775                1780                1785

Met Asp Glu Ala His Phe Thr Asp Pro Ala Ser Ile Ala Ala Arg
    1790                1795                1800

Gly Tyr Ile Ser Thr Lys Val Glu Leu Gly Glu Ala Ala Ala Ile
    1805                1810                1815

Phe Met Thr Ala Thr Pro Pro Gly Thr Ser Asp Pro Phe Pro Glu
    1820                1825                1830

Ser Asn Ser Pro Ile Ser Asp Leu Gln Thr Glu Ile Pro Asp Arg
    1835                1840                1845

Ala Trp Asn Ser Gly Tyr Glu Trp Ile Thr Glu Tyr Thr Gly Lys
    1850                1855                1860
```

```
Thr Val Trp Phe Val Pro Ser Val Lys Met Gly Asn Glu Ile Ala
1865             1870                 1875

Leu Cys Leu Gln Arg Ala Gly Lys Lys Val Gln Leu Asn Arg
    1880             1885                 1890

Lys Ser Tyr Glu Thr Glu Tyr Pro Lys Cys Lys Asn Asp Asp Trp
    1895             1900                 1905

Asp Phe Val Ile Thr Thr Asp Ile Ser Glu Met Gly Ala Asn Phe
    1910             1915                 1920

Lys Ala Ser Arg Val Ile Asp Ser Arg Lys Ser Val Lys Pro Thr
    1925             1930                 1935

Ile Ile Thr Glu Gly Glu Gly Arg Val Ile Leu Gly Glu Pro Ser
    1940             1945                 1950

Ala Val Thr Ala Ala Ser Ala Ala Gln Arg Arg Gly Arg Ile Gly
    1955             1960                 1965

Arg Asn Pro Ser Gln Val Gly Asp Glu Tyr Cys Tyr Gly Gly His
    1970             1975                 1980

Thr Asn Glu Asp Asp Ser Asn Phe Ala His Trp Thr Glu Ala Arg
    1985             1990                 1995

Ile Met Pro Asp Asn Ile Asn Met Pro Asn Gly Leu Ile Ala Gln
    2000             2005                 2010

Phe Tyr Gln Pro Glu Arg Glu Lys Val Tyr Thr Met Glu Gly Glu
    2015             2020                 2025

Tyr Arg Leu Arg Gly Glu Glu Arg Lys Asn Phe Leu Glu Leu Leu
    2030             2035                 2040

Arg Thr Ala Asp Leu Pro Val Trp Leu Ala Tyr Lys Val Ala Ala
    2045             2050                 2055

Ala Gly Val Ser Tyr His Asp Arg Arg Trp Cys Phe Asp Gly Pro
    2060             2065                 2070

Arg Thr Asn Thr Ile Leu Glu Asp Asn Asn Glu Val Glu Val Ile
    2075             2080                 2085

Thr Lys Leu Gly Glu Arg Lys Ile Leu Arg Pro Arg Trp Ile Asp
    2090             2095                 2100

Ala Arg Val Tyr Ser Asp His Gln Ala Leu Lys Ala Phe Lys Asp
    2105             2110                 2115

Phe Ala Ser Gly Lys Arg Ser Gln Ile Gly Leu Ile Glu Val Leu
    2120             2125                 2130

Gly Lys Met Pro Glu His Phe Met Gly Lys Thr Trp Glu Ala Leu
    2135             2140                 2145

Asp Thr Met Tyr Val Val Ala Thr Ala Glu Lys Gly Gly Arg Ala
    2150             2155                 2160

His Arg Met Ala Leu Glu Glu Leu Pro Asp Ala Leu Gln Thr Ile
    2165             2170                 2175

Ala Leu Ile Ala Leu Leu Ser Val Met Thr Met Gly Val Phe Phe
    2180             2185                 2190

Leu Leu Met Gln Arg Lys Gly Ile Gly Lys Ile Gly Leu Gly Gly
    2195             2200                 2205

Ala Val Leu Gly Val Ala Thr Phe Phe Cys Trp Met Ala Glu Val
    2210             2215                 2220

Pro Gly Thr Lys Ile Ala Gly Met Leu Leu Leu Ser Leu Leu Leu
    2225             2230                 2235

Met Ile Val Leu Ile Pro Glu Pro Glu Lys Gln Arg Ser Gln Thr
    2240             2245                 2250
```

```
Asp Asn Gln Leu Ala Val Phe Leu Ile Cys Val Met Thr Leu Val
2255                2260                2265

Ser Ala Val Ala Ala Asn Glu Met Gly Trp Leu Asp Lys Thr Lys
2270                2275                2280

Ser Asp Ile Ser Ser Leu Phe Gly Gln Arg Ile Glu Val Lys Glu
2285                2290                2295

Asn Phe Ser Met Gly Glu Phe Leu Leu Asp Leu Arg Pro Ala Thr
2300                2305                2310

Ala Trp Ser Leu Tyr Ala Val Thr Thr Ala Val Leu Thr Pro Leu
2315                2320                2325

Leu Lys His Leu Ile Thr Ser Asp Tyr Ile Asn Thr Ser Leu Thr
2330                2335                2340

Ser Ile Asn Val Gln Ala Ser Ala Leu Phe Thr Leu Ala Arg Gly
2345                2350                2355

Phe Pro Phe Val Asp Val Gly Val Ser Ala Leu Leu Leu Ala Ala
2360                2365                2370

Gly Cys Trp Gly Gln Val Thr Leu Thr Val Thr Val Thr Ala Ala
2375                2380                2385

Thr Leu Leu Phe Cys His Tyr Ala Tyr Met Val Pro Gly Trp Gln
2390                2395                2400

Ala Glu Ala Met Arg Ser Ala Gln Arg Arg Thr Ala Ala Gly Ile
2405                2410                2415

Met Lys Asn Ala Val Val Asp Gly Ile Val Ala Thr Asp Val Pro
2420                2425                2430

Glu Leu Glu Arg Thr Thr Pro Ile Met Gln Lys Lys Val Gly Gln
2435                2440                2445

Ile Met Leu Ile Leu Val Ser Leu Ala Ala Val Val Val Asn Pro
2450                2455                2460

Ser Val Lys Thr Val Arg Glu Ala Gly Ile Leu Ile Thr Ala Ala
2465                2470                2475

Ala Val Thr Leu Trp Glu Asn Gly Ala Ser Ser Val Trp Asn Ala
2480                2485                2490

Thr Thr Ala Ile Gly Leu Cys His Ile Met Arg Gly Gly Trp Leu
2495                2500                2505

Ser Cys Leu Ser Ile Thr Trp Thr Leu Ile Lys Asn Met Glu Lys
2510                2515                2520

Pro Gly Leu Lys Arg Gly Gly Ala Lys Gly Arg Thr Leu Gly Glu
2525                2530                2535

Val Trp Lys Glu Arg Leu Asn Gln Met Thr Lys Glu Glu Phe Thr
2540                2545                2550

Arg Tyr Arg Lys Glu Ala Ile Ile Glu Val Asp Arg Ser Ala Ala
2555                2560                2565

Lys His Ala Arg Lys Glu Gly Asn Val Thr Gly Gly His Ser Val
2570                2575                2580

Ser Arg Gly Thr Ala Lys Leu Arg Trp Leu Val Glu Arg Arg Phe
2585                2590                2595

Leu Glu Pro Val Gly Lys Val Ile Asp Leu Gly Cys Gly Arg Gly
2600                2605                2610

Gly Trp Cys Tyr Tyr Met Ala Thr Gln Lys Arg Val Gln Glu Val
2615                2620                2625

Arg Gly Tyr Thr Lys Gly Gly Pro Gly His Glu Glu Pro Gln Leu
2630                2635                2640

Val Gln Ser Tyr Gly Trp Asn Ile Val Thr Met Lys Ser Gly Val
```

```
                2645                2650                2655

Asp Val Phe Tyr Arg Pro Ser Glu Cys Cys Asp Thr Leu Leu Cys
            2660                2665                2670

Asp Ile Gly Glu Ser Ser Ser Ala Glu Val Glu Glu His Arg
        2675                2680                2685

Thr Ile Arg Val Leu Glu Met Val Glu Asp Trp Leu His Arg Gly
            2690                2695                2700

Pro Arg Glu Phe Cys Val Lys Val Leu Cys Pro Tyr Met Pro Lys
            2705                2710                2715

Val Ile Glu Lys Met Glu Leu Leu Gln Arg Arg Tyr Gly Gly Gly
            2720                2725                2730

Leu Val Arg Asn Pro Leu Ser Arg Asn Ser Thr His Glu Met Tyr
            2735                2740                2745

Trp Val Ser Arg Ala Ser Gly Asn Val His Ser Val Asn Met
            2750                2755                2760

Thr Ser Gln Val Leu Leu Gly Arg Met Glu Lys Arg Thr Trp Lys
            2765                2770                2775

Gly Pro Gln Tyr Glu Glu Asp Val Asn Leu Gly Ser Gly Thr Arg
            2780                2785                2790

Ala Val Gly Lys Pro Leu Leu Asn Ser Asp Thr Ser Lys Ile Asn
            2795                2800                2805

Asn Arg Ile Glu Arg Leu Arg Arg Glu Tyr Ser Ser Thr Trp His
            2810                2815                2820

His Asp Glu Asn His Pro Tyr Arg Thr Trp Asn Tyr His Gly Ser
            2825                2830                2835

Tyr Asp Val Lys Pro Thr Gly Ser Ala Ser Ser Leu Val Asn Gly
            2840                2845                2850

Val Val Arg Leu Leu Ser Lys Pro Trp Asp Thr Ile Thr Asn Val
            2855                2860                2865

Thr Thr Met Ala Met Thr Asp Thr Thr Pro Phe Gly Gln Gln Arg
            2870                2875                2880

Val Phe Lys Glu Lys Val Asp Thr Lys Ala Pro Glu Pro Pro Glu
            2885                2890                2895

Gly Ala Lys Tyr Val Leu Asn Glu Thr Thr Asn Trp Leu Trp Ala
            2900                2905                2910

Phe Leu Ala Arg Glu Lys Arg Pro Arg Met Cys Ser Arg Glu Glu
            2915                2920                2925

Phe Ile Arg Lys Val Asn Ser Asn Ala Ala Leu Gly Ala Met Phe
            2930                2935                2940

Glu Glu Gln Asn Gln Trp Arg Ser Ala Arg Glu Ala Val Glu Asp
            2945                2950                2955

Pro Lys Phe Trp Glu Met Val Asp Glu Glu Arg Glu Ala His Leu
            2960                2965                2970

Arg Gly Glu Cys His Thr Cys Ile Tyr Asn Met Met Gly Lys Arg
            2975                2980                2985

Glu Lys Lys Pro Gly Glu Phe Gly Lys Ala Lys Gly Ser Arg Ala
            2990                2995                3000

Ile Trp Phe Met Trp Leu Gly Ala Arg Phe Leu Glu Phe Glu Ala
            3005                3010                3015

Leu Gly Phe Leu Asn Glu Asp His Trp Leu Gly Arg Lys Asn Ser
            3020                3025                3030

Gly Gly Gly Val Glu Gly Leu Gly Leu Gln Lys Leu Gly Tyr Ile
            3035                3040                3045
```

-continued

```
Leu Arg Glu Val Gly Thr Arg Pro Gly Gly Lys Ile Tyr Ala Asp
    3050                3055                3060

Asp Thr Ala Gly Trp Asp Thr Arg Ile Thr Arg Ala Asp Leu Glu
    3065                3070                3075

Asn Glu Ala Lys Val Leu Glu Leu Leu Asp Gly Glu His Arg Arg
    3080                3085                3090

Leu Ala Arg Ala Ile Ile Glu Leu Thr Tyr Arg His Lys Val Val
    3095                3100                3105

Lys Val Met Arg Pro Ala Ala Asp Gly Arg Thr Val Met Asp Val
    3110                3115                3120

Ile Ser Arg Glu Asp Gln Arg Gly Ser Gly Gln Val Val Thr Tyr
    3125                3130                3135

Ala Leu Asn Thr Phe Thr Asn Leu Ala Val Gln Leu Val Arg Met
    3140                3145                3150

Met Glu Gly Glu Gly Val Ile Gly Pro Asp Asp Val Glu Lys Leu
    3155                3160                3165

Thr Lys Gly Lys Gly Pro Lys Val Arg Thr Trp Leu Phe Glu Asn
    3170                3175                3180

Gly Glu Glu Arg Leu Ser Arg Met Ala Val Ser Gly Asp Asp Cys
    3185                3190                3195

Val Val Lys Pro Leu Asp Asp Arg Phe Ala Thr Ser Leu His Phe
    3200                3205                3210

Leu Asn Ala Met Ser Lys Val Arg Lys Asp Ile Gln Glu Trp Lys
    3215                3220                3225

Pro Ser Thr Gly Trp Tyr Asp Trp Gln Gln Val Pro Phe Cys Ser
    3230                3235                3240

Asn His Phe Thr Glu Leu Ile Met Lys Asp Gly Arg Thr Leu Val
    3245                3250                3255

Val Pro Cys Arg Gly Gln Asp Glu Leu Val Gly Arg Ala Arg Ile
    3260                3265                3270

Ser Pro Gly Ala Gly Trp Asn Val Arg Asp Thr Ala Cys Leu Ala
    3275                3280                3285

Lys Ser Tyr Ala Gln Met Trp Leu Leu Leu Tyr Phe His Arg Arg
    3290                3295                3300

Asp Leu Arg Leu Met Ala Asn Ala Ile Cys Ser Ala Val Pro Val
    3305                3310                3315

Asn Trp Val Pro Thr Gly Arg Thr Thr Trp Ser Ile His Ala Gly
    3320                3325                3330

Gly Glu Trp Met Thr Thr Glu Asp Met Leu Glu Val Trp Asn Arg
    3335                3340                3345

Val Trp Ile Glu Glu Asn Glu Trp Met Glu Asp Lys Thr Pro Val
    3350                3355                3360

Glu Lys Trp Ser Asp Val Pro Tyr Ser Gly Lys Arg Glu Asp Ile
    3365                3370                3375

Trp Cys Gly Ser Leu Ile Gly Thr Arg Ala Arg Ala Thr Trp Ala
    3380                3385                3390

Glu Asn Ile Gln Val Ala Ile Asn Gln Val Arg Ala Ile Ile Gly
    3395                3400                3405

Asp Glu Lys Tyr Val Asp Tyr Met Ser Ser Leu Lys Arg Tyr Glu
    3410                3415                3420

Asp Thr Thr Leu Val Glu Asp Thr Val Leu
    3425                3430
```

<210> SEQ ID NO 3
<211> LENGTH: 37
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 3
tagcacgaag aattcgatgt ctaagaaacc aggaggg                          37

<210> SEQ ID NO 4
<211> LENGTH: 50
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 4
aagttagccc gggttaatgc tcctacgctg gcgatcaggc caatcaggac             50

<210> SEQ ID NO 5
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 5
agtagttcgc ctgtgtgagc tgacaaac                                    28

<210> SEQ ID NO 6
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 6
agatcctgtg ttctcgcacc accagccac                                   29

<210> SEQ ID NO 7
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 7
ggatggatgc twggkagcaa c                                           21

<210> SEQ ID NO 8
<211> LENGTH: 19
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 8
ccatccaagc ctccacatc                                              19

<210> SEQ ID NO 9
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE -continued

<400> SEQUENCE: 9
tggatgggat ccaatatgcg tgataggtcc                                          30

<210> SEQ ID NO 10
<211> LENGTH: 39
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 10
aaaagggtca atggtaccag cattttaagc attcacgtt                                39

<210> SEQ ID NO 11
<211> LENGTH: 36
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 11
tagcacgaag aattcgatgt ctaaaaacca ggaggg                                   36

<210> SEQ ID NO 12
<211> LENGTH: 3433
<212> TYPE: PRT
<213> ORGANISM: West Nile virus strain NY99-flamingo382-99

<400> SEQUENCE: 12

Met Ser Lys Lys Pro Gly Gly Pro Gly Lys Ser Arg Ala Val Asn Met
1               5                   10                  15

Leu Lys Arg Gly Met Pro Arg Val Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
    130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
        195                 200                 205

His Ser Arg Arg Ser Arg Arg Ser Leu Thr Val Gln Thr His Gly Glu
    210                 215                 220

-continued

```
Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
            245                 250                 255

Tyr Ala Leu Val Ala Val Ile Gly Trp Met Leu Gly Ser Asn Thr
        260                 265                 270

Met Gln Arg Val Val Phe Val Val Leu Leu Leu Val Ala Pro Ala
    275                 280                 285

Tyr Ser Phe Asn Cys Leu Gly Met Ser Asn Arg Asp Phe Leu Glu Gly
290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Glu Val Arg Ser Tyr Cys Tyr Leu
            340                 345                 350

Ala Thr Val Ser Asp Leu Ser Thr Lys Ala Ala Cys Pro Thr Met Gly
        355                 360                 365

Glu Ala His Asn Asp Lys Arg Ala Asp Pro Ala Phe Val Cys Arg Gln
    370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Ser Thr Lys Ala Ile
                405                 410                 415

Gly Arg Thr Ile Leu Lys Glu Asn Ile Lys Tyr Glu Val Ala Ile Phe
            420                 425                 430

Val His Gly Pro Thr Thr Val Glu Ser His Gly Asn Tyr Ser Thr Gln
        435                 440                 445

Val Gly Ala Thr Gln Ala Gly Arg Phe Ser Ile Thr Pro Ala Ala Pro
    450                 455                 460

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
                485                 490                 495

Gly Thr Lys Thr Phe Leu Val His Arg Glu Trp Phe Met Asp Leu Asn
            500                 505                 510

Leu Pro Trp Ser Ser Ala Gly Ser Thr Val Trp Arg Asn Arg Glu Thr
        515                 520                 525

Leu Met Glu Phe Glu Glu Pro His Ala Thr Lys Gln Ser Val Ile Ala
    530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
                565                 570                 575

Lys Cys Arg Val Lys Met Glu Lys Leu Gln Leu Lys Gly Thr Thr Tyr
            580                 585                 590

Gly Val Cys Ser Lys Ala Phe Lys Phe Leu Gly Thr Pro Ala Asp Thr
        595                 600                 605

Gly His Gly Thr Val Val Leu Glu Leu Gln Tyr Thr Gly Thr Asp Gly
    610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
```

-continued

```
            645                 650                 655
Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
            675                 680                 685

Lys Ser Gly Ser Ser Ile Gly Lys Ala Phe Thr Thr Thr Leu Lys Gly
            690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                    725                 730                 735

Gly Gly Ala Phe Arg Ser Leu Phe Gly Gly Met Ser Trp Ile Thr Gln
                    740                 745                 750

Gly Leu Leu Gly Ala Leu Leu Leu Trp Met Gly Ile Asn Ala Arg Asp
            755                 760                 765

Arg Ser Ile Ala Leu Thr Phe Leu Ala Val Gly Gly Val Leu Leu Phe
            770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
                    805                 810                 815

Glu Ala Trp Met Asp Arg Tyr Lys Tyr Tyr Pro Glu Thr Pro Gln Gly
                    820                 825                 830

Leu Ala Lys Ile Ile Gln Lys Ala His Lys Glu Gly Val Cys Gly Leu
            835                 840                 845

Arg Ser Val Ser Arg Leu Glu His Gln Met Trp Glu Ala Val Lys Asp
            850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
                    885                 890                 895

Ala Thr Thr Glu Lys Leu Glu Ile Gly Trp Lys Ala Trp Gly Lys Ser
                    900                 905                 910

Ile Leu Phe Ala Pro Glu Leu Ala Asn Asn Thr Phe Val Val Asp Gly
            915                 920                 925

Pro Glu Thr Lys Glu Cys Pro Thr Gln Asn Arg Ala Trp Asn Ser Leu
            930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
                    965                 970                 975

Thr Ala Val Lys Asn Asn Leu Ala Ile His Ser Asp Leu Ser Tyr Trp
                    980                 985                 990

Ile Glu Ser Arg Leu Asn Asp Thr Trp Lys Leu Glu Arg Ala Val Leu
            995                 1000                1005

Gly Glu Val Lys Ser Cys Thr Trp Pro Glu Thr His Thr Leu Trp
            1010                1015                1020

Gly Asp Gly Ile Leu Glu Ser Asp Leu Ile Ile Pro Val Thr Leu
            1025                1030                1035

Ala Gly Pro Arg Ser Asn His Asn Arg Arg Pro Gly Tyr Lys Thr
            1040                1045                1050

Gln Asn Gln Gly Pro Trp Asp Glu Gly Arg Val Glu Ile Asp Phe
            1055                1060                1065
```

-continued

```
Asp Tyr Cys Pro Gly Thr Thr Val Thr Leu Ser Glu Ser Cys Gly
    1070                1075                1080

His Arg Gly Pro Ala Thr Arg Thr Thr Thr Glu Ser Gly Lys Leu
    1085                1090                1095

Ile Thr Asp Trp Cys Cys Arg Ser Cys Thr Leu Pro Pro Leu Arg
    1100                1105                1110

Tyr Gln Thr Asp Ser Gly Cys Trp Tyr Gly Met Glu Ile Arg Pro
    1115                1120                1125

Gln Arg His Asp Glu Lys Thr Leu Val Gln Ser Gln Val Asn Ala
    1130                1135                1140

Tyr Asn Ala Asp Met Ile Asp Pro Phe Gln Leu Gly Leu Leu Val
    1145                1150                1155

Val Phe Leu Ala Thr Gln Glu Val Leu Arg Lys Arg Trp Thr Ala
    1160                1165                1170

Lys Ile Ser Met Pro Ala Ile Leu Ile Ala Leu Leu Val Leu Val
    1175                1180                1185

Phe Gly Gly Ile Thr Tyr Thr Asp Val Leu Arg Tyr Val Ile Leu
    1190                1195                1200

Val Gly Ala Ala Phe Ala Glu Ser Asn Ser Gly Gly Asp Val Val
    1205                1210                1215

His Leu Ala Leu Met Ala Thr Phe Lys Ile Gln Pro Val Phe Met
    1220                1225                1230

Val Ala Ser Phe Leu Lys Ala Arg Trp Thr Asn Gln Glu Asn Ile
    1235                1240                1245

Leu Leu Met Leu Ala Ala Val Phe Phe Gln Met Ala Tyr His Asp
    1250                1255                1260

Ala Arg Gln Ile Leu Leu Trp Glu Ile Pro Asp Val Leu Asn Ser
    1265                1270                1275

Leu Ala Val Ala Trp Met Ile Leu Arg Ala Ile Thr Phe Thr Thr
    1280                1285                1290

Thr Ser Asn Val Val Pro Leu Leu Ala Leu Leu Thr Pro Gly
    1295                1300                1305

Leu Arg Cys Leu Asn Leu Asp Val Tyr Arg Ile Leu Leu Leu Met
    1310                1315                1320

Val Gly Ile Gly Ser Leu Ile Arg Glu Lys Arg Ser Ala Ala Ala
    1325                1330                1335

Lys Lys Lys Gly Ala Ser Leu Leu Cys Leu Ala Leu Ala Ser Thr
    1340                1345                1350

Gly Leu Phe Asn Pro Met Ile Leu Ala Ala Gly Leu Ile Ala Cys
    1355                1360                1365

Asp Pro Asn Arg Lys Arg Gly Trp Pro Ala Thr Glu Val Met Thr
    1370                1375                1380

Ala Val Gly Leu Met Phe Ala Ile Val Gly Gly Leu Ala Glu Leu
    1385                1390                1395

Asp Ile Asp Ser Met Ala Ile Pro Met Thr Ile Ala Gly Leu Met
    1400                1405                1410

Phe Ala Ala Phe Val Ile Ser Gly Lys Ser Thr Asp Met Trp Ile
    1415                1420                1425

Glu Arg Thr Ala Asp Ile Ser Trp Glu Ser Asp Ala Glu Ile Thr
    1430                1435                1440

Gly Ser Ser Glu Arg Val Asp Val Arg Leu Asp Asp Gly Asn
    1445                1450                1455
```

-continued

```
Phe Gln Leu Met Asn Asp Pro Gly Ala Pro Trp Lys Ile Trp Met
    1460                1465                1470
Leu Arg Met Val Cys Leu Ala Ile Ser Ala Tyr Thr Pro Trp Ala
    1475                1480                1485
Ile Leu Pro Ser Val Val Gly Phe Trp Ile Thr Leu Gln Tyr Thr
    1490                1495                1500
Lys Arg Gly Gly Val Leu Trp Asp Thr Pro Ser Pro Lys Glu Tyr
    1505                1510                1515
Lys Lys Gly Asp Thr Thr Thr Gly Val Tyr Arg Ile Met Thr Arg
    1520                1525                1530
Gly Leu Leu Gly Ser Tyr Gln Ala Gly Ala Gly Val Met Val Glu
    1535                1540                1545
Gly Val Phe His Thr Leu Trp His Thr Thr Lys Gly Ala Ala Leu
    1550                1555                1560
Met Ser Gly Glu Gly Arg Leu Asp Pro Tyr Trp Gly Ser Val Lys
    1565                1570                1575
Glu Asp Arg Leu Cys Tyr Gly Gly Pro Trp Lys Leu Gln His Lys
    1580                1585                1590
Trp Asn Gly Gln Asp Glu Val Gln Met Ile Val Val Glu Pro Gly
    1595                1600                1605
Lys Asn Val Lys Asn Val Gln Thr Lys Pro Gly Val Phe Lys Thr
    1610                1615                1620
Pro Glu Gly Glu Ile Gly Ala Val Thr Leu Asp Phe Pro Thr Gly
    1625                1630                1635
Thr Ser Gly Ser Pro Ile Val Asp Lys Asn Gly Asp Val Ile Gly
    1640                1645                1650
Leu Tyr Gly Asn Gly Val Ile Met Pro Asn Gly Ser Tyr Ile Ser
    1655                1660                1665
Ala Ile Val Gln Gly Glu Arg Met Asp Glu Pro Ile Pro Ala Gly
    1670                1675                1680
Phe Glu Pro Glu Met Leu Arg Lys Lys Gln Ile Thr Val Leu Asp
    1685                1690                1695
Leu His Pro Gly Ala Gly Lys Thr Arg Arg Ile Leu Pro Gln Ile
    1700                1705                1710
Ile Lys Glu Ala Ile Asn Arg Arg Leu Arg Thr Ala Val Leu Ala
    1715                1720                1725
Pro Thr Arg Val Val Ala Ala Glu Met Ala Glu Ala Leu Arg Gly
    1730                1735                1740
Leu Pro Ile Arg Tyr Gln Thr Ser Ala Val Pro Arg Glu His Asn
    1745                1750                1755
Gly Asn Glu Ile Val Asp Val Met Cys His Ala Thr Leu Thr His
    1760                1765                1770
Arg Leu Met Ser Pro His Arg Val Pro Asn Tyr Asn Leu Phe Val
    1775                1780                1785
Met Asp Glu Ala His Phe Thr Asp Pro Ala Ser Ile Ala Ala Arg
    1790                1795                1800
Gly Tyr Ile Ser Thr Lys Val Glu Leu Gly Glu Ala Ala Ala Ile
    1805                1810                1815
Phe Met Thr Ala Thr Pro Pro Gly Thr Ser Asp Pro Phe Pro Glu
    1820                1825                1830
Ser Asn Ser Pro Ile Ser Asp Leu Gln Thr Glu Ile Pro Asp Arg
    1835                1840                1845
Ala Trp Asn Ser Gly Tyr Glu Trp Ile Thr Glu Tyr Thr Gly Lys
```

-continued

```
              1850                1855                1860
Thr Val  Trp Phe Val Pro Ser  Val Lys Met Gly Asn  Glu Ile Ala
    1865                1870                1875

Leu Cys  Leu Gln Arg Ala Gly  Lys Lys Val Val Gln  Leu Asn Arg
    1880                1885                1890

Lys Ser  Tyr Glu Thr Glu Tyr  Pro Lys Cys Lys Asn  Asp Asp Trp
    1895                1900                1905

Asp Phe  Val Ile Thr Thr Asp  Ile Ser Glu Met Gly  Ala Asn Phe
    1910                1915                1920

Lys Ala  Ser Arg Val Ile Asp  Ser Arg Lys Ser Val  Lys Pro Thr
    1925                1930                1935

Ile Ile  Thr Glu Gly Glu Gly  Arg Val Ile Leu Gly  Glu Pro Ser
    1940                1945                1950

Ala Val  Thr Ala Ala Ser Ala  Ala Gln Arg Arg Gly  Arg Ile Gly
    1955                1960                1965

Arg Asn  Pro Ser Gln Val Gly  Asp Glu Tyr Cys Tyr  Gly Gly His
    1970                1975                1980

Thr Asn  Glu Asp Asp Ser Asn  Phe Ala His Trp Thr  Glu Ala Arg
    1985                1990                1995

Ile Met  Leu Asp Asn Ile Asn  Met Pro Asn Gly Leu  Ile Ala Gln
    2000                2005                2010

Phe Tyr  Gln Pro Glu Arg Glu  Lys Val Tyr Thr Met  Asp Gly Glu
    2015                2020                2025

Tyr Arg  Leu Arg Gly Glu Glu  Arg Lys Asn Phe Leu  Glu Leu Leu
    2030                2035                2040

Arg Thr  Ala Asp Leu Pro Val  Trp Leu Ala Tyr Lys  Val Ala Ala
    2045                2050                2055

Ala Gly  Val Ser Tyr His Asp  Arg Arg Trp Cys Phe  Asp Gly Pro
    2060                2065                2070

Arg Thr  Asn Thr Ile Leu Glu  Asp Asn Asn Glu Val  Glu Val Ile
    2075                2080                2085

Thr Lys  Leu Gly Glu Arg Lys  Ile Leu Arg Pro Arg  Trp Ile Asp
    2090                2095                2100

Ala Arg  Val Tyr Ser Asp His  Gln Ala Leu Lys Ala  Phe Lys Asp
    2105                2110                2115

Phe Ala  Ser Gly Lys Arg Ser  Gln Ile Gly Leu Ile  Glu Val Leu
    2120                2125                2130

Gly Lys  Met Pro Glu His Phe  Met Gly Lys Thr Trp  Glu Ala Leu
    2135                2140                2145

Asp Thr  Met Tyr Val Val Ala  Thr Ala Glu Lys Gly  Gly Arg Ala
    2150                2155                2160

His Arg  Met Ala Leu Glu Glu  Leu Pro Asp Ala Leu  Gln Thr Ile
    2165                2170                2175

Ala Leu  Ile Ala Leu Leu Ser  Val Met Thr Met Gly  Val Phe Phe
    2180                2185                2190

Leu Leu  Met Gln Arg Lys Gly  Ile Gly Lys Ile Gly  Leu Gly Gly
    2195                2200                2205

Ala Val  Leu Gly Val Ala Thr  Phe Phe Cys Trp Met  Ala Glu Val
    2210                2215                2220

Pro Gly  Thr Lys Ile Ala Gly  Met Leu Leu Leu Ser  Leu Leu Leu
    2225                2230                2235

Met Ile  Val Leu Ile Pro Glu  Pro Glu Lys Gln Arg  Ser Gln Thr
    2240                2245                2250
```

-continued

```
Asp Asn Gln Leu Ala Val Phe Leu Ile Cys Val Met Thr Leu Val
2255                2260                2265

Ser Ala Val Ala Ala Asn Glu Met Gly Trp Leu Asp Lys Thr Lys
2270                2275                2280

Ser Asp Ile Ser Ser Leu Phe Gly Gln Arg Ile Glu Val Lys Glu
2285                2290                2295

Asn Phe Ser Met Gly Glu Phe Leu Leu Asp Leu Arg Pro Ala Thr
2300                2305                2310

Ala Trp Ser Leu Tyr Ala Val Thr Thr Ala Val Leu Thr Pro Leu
2315                2320                2325

Leu Lys His Leu Ile Thr Ser Asp Tyr Ile Asn Thr Ser Leu Thr
2330                2335                2340

Ser Ile Asn Val Gln Ala Ser Ala Leu Phe Thr Leu Ala Arg Gly
2345                2350                2355

Phe Pro Phe Val Asp Val Gly Val Ser Ala Leu Leu Leu Ala Ala
2360                2365                2370

Gly Cys Trp Gly Gln Val Thr Leu Thr Val Thr Val Thr Ala Ala
2375                2380                2385

Thr Leu Leu Phe Cys His Tyr Ala Tyr Met Val Pro Gly Trp Gln
2390                2395                2400

Ala Glu Ala Met Arg Ser Ala Gln Arg Arg Thr Ala Ala Gly Ile
2405                2410                2415

Met Lys Asn Ala Val Val Asp Gly Ile Val Ala Thr Asp Val Pro
2420                2425                2430

Glu Leu Glu Arg Thr Thr Pro Ile Met Gln Lys Lys Val Gly Gln
2435                2440                2445

Ile Met Leu Ile Leu Val Ser Leu Ala Ala Val Val Val Asn Pro
2450                2455                2460

Ser Val Lys Thr Val Arg Glu Ala Gly Ile Leu Ile Thr Ala Ala
2465                2470                2475

Ala Val Thr Leu Trp Glu Asn Gly Ala Ser Ser Val Trp Asn Ala
2480                2485                2490

Thr Thr Ala Ile Gly Leu Cys His Ile Met Arg Gly Gly Trp Leu
2495                2500                2505

Ser Cys Leu Ser Ile Thr Trp Thr Leu Ile Lys Asn Met Glu Lys
2510                2515                2520

Pro Gly Leu Lys Arg Gly Gly Ala Lys Gly Arg Thr Leu Gly Glu
2525                2530                2535

Val Trp Lys Glu Arg Leu Asn Gln Met Thr Lys Glu Glu Phe Thr
2540                2545                2550

Arg Tyr Arg Lys Glu Ala Ile Ile Glu Val Asp Arg Ser Ala Ala
2555                2560                2565

Lys His Ala Arg Lys Glu Gly Asn Val Thr Gly Gly His Pro Val
2570                2575                2580

Ser Arg Gly Thr Ala Lys Leu Arg Trp Leu Val Glu Arg Arg Phe
2585                2590                2595

Leu Glu Pro Val Gly Lys Val Ile Asp Leu Gly Cys Gly Arg Gly
2600                2605                2610

Gly Trp Cys Tyr Tyr Met Ala Thr Gln Lys Arg Val Gln Glu Val
2615                2620                2625

Arg Gly Tyr Thr Lys Gly Gly Pro Gly His Glu Glu Pro Gln Leu
2630                2635                2640
```

-continued

Val Gln Ser Tyr Gly Trp Asn Ile Val Thr Met Lys Ser Gly Val
2645                2650                2655

Asp Val Phe Tyr Arg Pro Ser Glu Cys Cys Asp Thr Leu Leu Cys
2660                2665                2670

Asp Ile Gly Glu Ser Ser Ser Ala Glu Val Glu Glu His Arg
2675                2680                2685

Thr Ile Arg Val Leu Glu Met Val Glu Asp Trp Leu His Arg Gly
2690                2695                2700

Pro Arg Glu Phe Cys Val Lys Val Leu Cys Pro Tyr Met Pro Lys
2705                2710                2715

Val Ile Glu Lys Met Glu Leu Leu Gln Arg Arg Tyr Gly Gly Gly
2720                2725                2730

Leu Val Arg Asn Pro Leu Ser Arg Asn Ser Thr His Glu Met Tyr
2735                2740                2745

Trp Val Ser Arg Ala Ser Gly Asn Val Val His Ser Val Asn Met
2750                2755                2760

Thr Ser Gln Val Leu Leu Gly Arg Met Glu Lys Arg Thr Trp Lys
2765                2770                2775

Gly Pro Gln Tyr Glu Glu Asp Val Asn Leu Gly Ser Gly Thr Arg
2780                2785                2790

Ala Val Gly Lys Pro Leu Leu Asn Ser Asp Thr Ser Lys Ile Lys
2795                2800                2805

Asn Arg Ile Glu Arg Leu Arg Arg Glu Tyr Ser Ser Thr Trp His
2810                2815                2820

His Asp Glu Asn His Pro Tyr Arg Thr Trp Asn Tyr His Gly Ser
2825                2830                2835

Tyr Asp Val Lys Pro Thr Gly Ser Ala Ser Ser Leu Val Asn Gly
2840                2845                2850

Val Val Arg Leu Leu Ser Lys Pro Trp Asp Thr Ile Thr Asn Val
2855                2860                2865

Thr Thr Met Ala Met Thr Asp Thr Thr Pro Phe Gly Gln Gln Arg
2870                2875                2880

Val Phe Lys Glu Lys Val Asp Thr Lys Ala Pro Glu Pro Pro Glu
2885                2890                2895

Gly Val Lys Tyr Val Leu Asn Glu Thr Thr Asn Trp Leu Trp Ala
2900                2905                2910

Phe Leu Ala Arg Glu Lys Arg Pro Arg Met Cys Ser Arg Glu Glu
2915                2920                2925

Phe Ile Arg Lys Val Asn Ser Asn Ala Ala Leu Gly Ala Met Phe
2930                2935                2940

Glu Glu Gln Asn Gln Trp Arg Ser Ala Arg Glu Ala Val Glu Asp
2945                2950                2955

Pro Lys Phe Trp Glu Met Val Asp Glu Glu Arg Glu Ala His Leu
2960                2965                2970

Arg Gly Glu Cys His Thr Cys Ile Tyr Asn Met Met Gly Lys Arg
2975                2980                2985

Glu Lys Lys Pro Gly Glu Phe Gly Lys Ala Lys Gly Ser Arg Ala
2990                2995                3000

Ile Trp Phe Met Trp Leu Gly Ala Arg Phe Leu Glu Phe Glu Ala
3005                3010                3015

Leu Gly Phe Leu Asn Glu Asp His Trp Leu Gly Arg Lys Asn Ser
3020                3025                3030

Gly Gly Gly Val Glu Gly Leu Gly Leu Gln Lys Leu Gly Tyr Ile

-continued

```
                3035                3040                3045

Leu Arg Glu Val Gly Thr Arg Pro Gly Gly Lys Ile Tyr Ala Asp
    3050                3055                3060

Asp Thr Ala Gly Trp Asp Thr Arg Ile Thr Arg Ala Asp Leu Glu
    3065                3070                3075

Asn Glu Ala Lys Val Leu Glu Leu Leu Asp Gly Glu His Arg Arg
    3080                3085                3090

Leu Ala Arg Ala Ile Ile Glu Leu Thr Tyr Arg His Lys Val Val
    3095                3100                3105

Lys Val Met Arg Pro Ala Ala Asp Gly Arg Thr Val Met Asp Val
    3110                3115                3120

Ile Ser Arg Glu Asp Gln Arg Gly Ser Gly Gln Val Val Thr Tyr
    3125                3130                3135

Ala Leu Asn Thr Phe Thr Asn Leu Ala Val Gln Leu Val Arg Met
    3140                3145                3150

Met Glu Gly Glu Gly Val Ile Gly Pro Asp Asp Val Glu Lys Leu
    3155                3160                3165

Thr Lys Gly Lys Gly Pro Lys Val Arg Thr Trp Leu Phe Glu Asn
    3170                3175                3180

Gly Glu Glu Arg Leu Ser Arg Met Ala Val Ser Gly Asp Asp Cys
    3185                3190                3195

Val Val Lys Pro Leu Asp Asp Arg Phe Ala Thr Ser Leu His Phe
    3200                3205                3210

Leu Asn Ala Met Ser Lys Val Arg Lys Asp Ile Gln Glu Trp Lys
    3215                3220                3225

Pro Ser Thr Gly Trp Tyr Asp Trp Gln Gln Val Pro Phe Cys Ser
    3230                3235                3240

Asn His Phe Thr Glu Leu Ile Met Lys Asp Gly Arg Thr Leu Val
    3245                3250                3255

Val Pro Cys Arg Gly Gln Asp Glu Leu Val Gly Arg Ala Arg Ile
    3260                3265                3270

Ser Pro Gly Ala Gly Trp Asn Val Arg Asp Thr Ala Cys Leu Ala
    3275                3280                3285

Lys Ser Tyr Ala Gln Met Trp Leu Leu Leu Tyr Phe His Arg Arg
    3290                3295                3300

Asp Leu Arg Leu Met Ala Asn Ala Ile Cys Ser Ala Val Pro Val
    3305                3310                3315

Asn Trp Val Pro Thr Gly Arg Thr Thr Trp Ser Ile His Ala Gly
    3320                3325                3330

Gly Glu Trp Met Thr Thr Glu Asp Met Leu Glu Val Trp Asn Arg
    3335                3340                3345

Val Trp Ile Glu Glu Asn Glu Trp Met Glu Asp Lys Thr Pro Val
    3350                3355                3360

Glu Lys Trp Ser Asp Val Pro Tyr Ser Gly Lys Arg Glu Asp Ile
    3365                3370                3375

Trp Cys Gly Ser Leu Ile Gly Thr Arg Ala Arg Ala Thr Trp Ala
    3380                3385                3390

Glu Asn Ile Gln Val Ala Ile Asn Gln Val Arg Ala Ile Ile Gly
    3395                3400                3405
```

```
Asp Glu Lys Tyr Val Asp Tyr Met Ser Ser Leu Lys Arg Tyr Glu
    3410            3415               3420

Asp Thr Thr Leu Val Glu Asp Thr Val Leu
    3425            3430
```